United States Patent
Kumar et al.

(10) Patent No.: US 9,914,933 B2
(45) Date of Patent: Mar. 13, 2018

(54) ROOT-PREFERRED PROMOTER FROM A BRACHYPODIUM DISTACHYON METALLOTHIONEIN-LIKE GENE

(71) Applicant: Dow AgroSciences LLC, Indianapolis, IN (US)

(72) Inventors: Sandeep Kumar, Carmel, IN (US); Daren Hemingway, Westfield, IN (US); Carla Ausmus, Pasadena, MD (US); Andrew F. Worden, Indianapolis, IN (US); Andrew Asberry, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/097,345

(22) Filed: Apr. 13, 2016

(65) Prior Publication Data

US 2016/0304894 A1 Oct. 20, 2016

Related U.S. Application Data

(60) Provisional application No. 62/147,868, filed on Apr. 15, 2015.

(51) Int. Cl.
C12N 15/82 (2006.01)

(52) U.S. Cl.
CPC ................ *C12N 15/8227* (2013.01)

(58) Field of Classification Search
None
See application file for complete search history.

(56) References Cited

U.S. PATENT DOCUMENTS

2008/0227639 A1 9/2008 Wu
2015/0101083 A1 4/2015 Gupta et al.

FOREIGN PATENT DOCUMENTS

WO 2015051075 A1 4/2015

OTHER PUBLICATIONS

Ren et al. Functional analysis of the rice metallothionein gene OsMT2b promoter in transgenic *Arabidopsis* plants and rice germinated embryos. (2009) Plant Science; vol. 176; pp. 528-538.*
Li et al. A near-upstream element in a plant polyadenylation signal consists of more than six nucleotides. (1995) Plant Molecular Biology; vol. 28; pp. 927-934.*
Zhou et al. Structure, organization and expression of the metallotionein gene family in *Arabidopsis*. (1995) Mol. Gen. Genet.; vol. 248; pp. 318-328.*
Melanie Febrer et al., "An Integrated Physical, Genetic and Cytogenic Map of Brachypodium distachyon, a Model System for Grass Research" pLOS One, vol. 5, No. 10.
Mar. 10, 2009 "BD_ABa0009G19.f BD_ABa Brachypodium distachyon genomic clone BD_ABa0009G19 5', genomic survey sequence." XP002759447, retrieved from EBI accession No. EM_GSS:FI623744 Database Accession No. FI623744.
Solovyev VV, et al (2010) Identification of promoter regions and regulatory sites. Methods Mol Biol. 674, 57-83.
Chi-Nga C., et al., PlantPAN 2.0: an update of plant promoter analysis navigator for reconstructing transcriptional regulatory networks in plants, Nucleic Acids Res. 2015: gkv1035v1-gkv1035.

* cited by examiner

*Primary Examiner* — Cathy Kingdon Worley
(74) *Attorney, Agent, or Firm* — Sean M. Russell

(57) ABSTRACT

This disclosure concerns compositions and methods for promoting transcription of a nucleotide sequence in a plant or plant cell, employing a promoter from a *Brachypodium distachyon* metallothionein-like gene (mtl). Some embodiments relate to a promoter from a *Brachypodium distachyon* metallothionein-like gene (mtl) that functions in plants to promote transcription of operably linked nucleotide sequences.

15 Claims, 15 Drawing Sheets

FIGURE 2:

```
                          1                                                50
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    ------------------------------------------------------
SEQ ID NO:1      (1)    TTTCGTGTGCTTACTTGGGGCTTCCTTTGGGCCTGCGGAAGCAGACGGCG
                          51                                               100
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    ------------------------------------------------------
SEQ ID NO:1     (51)    TGCCAGCTGAGACCGTTGGTGGACAATGTGGATGGACGTCTAGCTTCGTG
                          101                                              150
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    ------------------------------------------------------
SEQ ID NO:1    (101)    GAAGGCCCTTCTCCTTTCCAAGGGAGGATGACTGGTGCTGGTCAAGTCCA
                          151                                              200
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    ------------------------------------------------------
SEQ ID NO:1    (151)    CCCTGACAGCGATGCCGGTCTACTCGATGATGTCACTCGACCTTTCGGAC
                          201                                              250
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    ------------------------------------------------------
SEQ ID NO:1    (201)    AAGATCATCAAGGGGTGGACAAGATCTGTCGTGGTTTCCTTTGGCGTGG
                          251                                              300
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7      (1)    --------------------GGGGGGCATTGTATGGTGGCTTGGGTCGTG
SEQ ID NO:1    (251)    TCAGAAGGACGCTAAAGGGGGGGGGCATTGTATGGTGGCTTGGGTCGTG
                          301                                              350
SEQ ID NO:11     (1)    ------------------------------------------------------
SEQ ID NO:10     (1)    ------------------------------------------------------
SEQ ID NO:9      (1)    ------------------------------------------------------
SEQ ID NO:8      (1)    ------------------------------------------------------
SEQ ID NO:7     (31)    GTGTGTTCGCCGAAGCCTTTCGGTGGACTCGGAATTCCAAATCTTCGCAT
SEQ ID NO:1    (301)    GTGTGTTCGCCGAAGCCTTTCGGTGGACTCGGAATTCCAAATCTTCGCAT
```

FIGURE 2 (Continued):

```
                      351                                              400
SEQ ID NO:11    (1)   --------------------------------------------------
SEQ ID NO:10    (1)   --------------------------------------------------
SEQ ID NO:9     (1)   --------------------------------------------------
SEQ ID NO:8     (1)   --------------------------------------------------
SEQ ID NO:7    (81)   GCTCAACGAGGCCTTGAGGGTCCGCTAGAGGTGGCTTGAGAGGGTGGACG
SEQ ID NO:1   (351)   GCTCAACGAGGCCTTGAGGGTCCGCTAGAGGTGGCTTGAGAGGGTGGACG
                      401                                              450
SEQ ID NO:11    (1)   --------------------------------------------------
SEQ ID NO:10    (1)   --------------------------------------------------
SEQ ID NO:9     (1)   --------------------------------------------------
SEQ ID NO:8     (1)   --------------------------------------------------
SEQ ID NO:7   (131)   ATTCCAAACCATGGGTCGGTTTCAAGGTTGAGACGCCCAGAGGTCTATGT
SEQ ID NO:1   (401)   ATTCCAAACCATGGGTCGGTTTCAAGGTTGAGACGCCCAGAGGTCTATGT
                      451                                              500
SEQ ID NO:11    (1)   --------------------------------------------------
SEQ ID NO:10    (1)   --------------------------------------------------
SEQ ID NO:9     (1)   --------------------------------------------------
SEQ ID NO:8     (1)   ---------------------CCTCTTTGGTGGGCGATGGCCGGAAGACCC
SEQ ID NO:7   (181)   TATCTTTGAGGCGGCCACTTCCTCTTTGGTGGGCGATGGCCGGAAGACCC
SEQ ID NO:1   (451)   TATCTTTGAGGCGGCCACTTCCTCTTTGGTGGGCGATGGCCGGAAGACCC
                      501                                              550
SEQ ID NO:11    (1)   --------------------------------------------------
SEQ ID NO:10    (1)   --------------------------------------------------
SEQ ID NO:9     (1)   --------------------------------------------------
SEQ ID NO:8    (31)   TCTTCTGGACCGATCGTTGGCTGCATGGCGTCTGTTTTCGAGATGCGTTC
SEQ ID NO:7   (231)   TCTTCTGGACCGATCGTTGGCTGCATGGCGTCTGTTTTCGAGATGCGTTC
SEQ ID NO:1   (501)   TCTTCTGGACCGATCGTTGGCTGCATGGCGTCTGTTTTCGAGATGCGTTC
                      551                                              600
SEQ ID NO:11    (1)   --------------------------------------------------
SEQ ID NO:10    (1)   --------------------------------------------------
SEQ ID NO:9     (1)   --------------------------------------------------
SEQ ID NO:8    (81)   CTGATCCTCGTGGGCCATGTTTGCCACAAGTTTTTGCGCACGCGCACAGT
SEQ ID NO:7   (281)   CTGATCCTCGTGGGCCATGTTTGCCACAAGTTTTTGCGCACGCGCACAGT
SEQ ID NO:1   (551)   CTGATCCTCGTGGGCCATGTTTGCCACAAGTTTTTGCGCACGCGCACAGT
                      601                                              650
SEQ ID NO:11    (1)   --------------------------------------------------
SEQ ID NO:10    (1)   --------------------------------------------------
SEQ ID NO:9     (1)   --------------------------------------------------
SEQ ID NO:8   (131)   GCGGGAGGCTCTGCATGGAGCGTGGACTGGCGACATGGGTCCAGACCTAA
SEQ ID NO:7   (331)   GCGGGAGGCTCTGCATGGAGCGTGGACTGGCGACATGGGTCCAGACCTAA
SEQ ID NO:1   (601)   GCGGGAGGCTCTGCATGGAGCGTGGACTGGCGACATGGGTCCAGACCTAA
                      651                                              700
SEQ ID NO:11    (1)   --------------------------------------------------
SEQ ID NO:10    (1)   --------------------------------------------------
SEQ ID NO:9     (1)   ------------------GTTCCTCACTCTCTGGGACTGGCTTCGTGG
SEQ ID NO:8   (181)   AGGGAAGCTACTCTTGAGGAGTTCCTCACTCTCTGGGACTGGCTTCGTGG
SEQ ID NO:7   (381)   AGGGAAGCTACTCTTGAGGAGTTCCTCACTCTCTGGGACTGGCTTCGTGG
SEQ ID NO:1   (651)   AGGGAAGCTACTCTTGAGGAGTTCCTCACTCTCTGGGACTGGCTTCGTGG
```

FIGURE 2 (Continued):

```
                          701                                                750
SEQ ID NO:11       (1)    --------------------------------------------------
SEQ ID NO:10       (1)    --------------------------------------------------
 SEQ ID NO:9      (31)    GGTCCAACTGGAAGAAGGGAGGGCCGACTCTCTTCATTGGAACTGGTCTC
 SEQ ID NO:8     (231)    GGTCCAACTGGAAGAAGGGAGGGCCGACTCTCTTCATTGGAACTGGTCTC
 SEQ ID NO:7     (431)    GGTCCAACTGGAAGAAGGGAGGGCCGACTCTCTTCATTGGAACTGGTCTC
 SEQ ID NO:1     (701)    GGTCCAACTGGAAGAAGGGAGGGCCGACTCTCTTCATTGGAACTGGTCTC
                          751                                                800
SEQ ID NO:11       (1)    --------------------------------------------------
SEQ ID NO:10       (1)    --------------------------------------------------
 SEQ ID NO:9      (81)    GTGGTGATAGTTACTCGGCAAAGACTGCTTATGCGAATCTCTTCACTGGC
 SEQ ID NO:8     (281)    GTGGTGATAGTTACTCGGCAAAGACTGCTTATGCGAATCTCTTCACTGGC
 SEQ ID NO:7     (481)    GTGGTGATAGTTACTCGGCAAAGACTGCTTATGCGAATCTCTTCACTGGC
 SEQ ID NO:1     (751)    GTGGTGATAGTTACTCGGCAAAGACTGCTTATGCGAATCTCTTCACTGGC
                          801                                                850
SEQ ID NO:11       (1)    --------------------------------------------------
SEQ ID NO:10       (1)    --------------------------------------------------
 SEQ ID NO:9     (131)    CGCATGGTTGACCCGTTAGCGGCTGAGATCTAGGGCTTCGGAGAGGTGTC
 SEQ ID NO:8     (331)    CGCATGGTTGACCCGTTAGCGGCTGAGATCTAGGGCTTCGGAGAGGTGTC
 SEQ ID NO:7     (531)    CGCATGGTTGACCCGTTAGCGGCTGAGATCTAGGGCTTCGGAGAGGTGTC
 SEQ ID NO:1     (801)    CGCATGGTTGACCCGTTAGCGGCTGAGATCTAGGGCTTCGGAGAGGTGTC
                          851                                                900
SEQ ID NO:11       (1)    --------------------------------------------------
SEQ ID NO:10       (1)    -------------------GTTCGAAATAGATGCTAGACGGCGGATCGC
 SEQ ID NO:9     (181)    GTTTCTTCGTCTGGCTCGCAGTTCGAAATAGATGCTAGACGGCGGATCGC
 SEQ ID NO:8     (381)    GTTTCTTCGTCTGGCTCGCAGTTCGAAATAGATGCTAGACGGCGGATCGC
 SEQ ID NO:7     (581)    GTTTCTTCGTCTGGCTCGCAGTTCGAAATAGATGCTAGACGGCGGATCGC
 SEQ ID NO:1     (851)    GTTTCTTCGTCTGGCTCGCAGTTCGAAATAGATGCTAGACGGCGGATCGC
                          901                                                950
SEQ ID NO:11       (1)    --------------------------------------------------
SEQ ID NO:10      (31)    TTGCGAGGCGTGGGCTTCCCCACCCTGACAAGTGTCAGGAGATGGAGACC
 SEQ ID NO:9     (231)    TTGCGAGGCGTGGGCTTCCCCACCCTGACAAGTGTCAGGAGATGGAGACC
 SEQ ID NO:8     (431)    TTGCGAGGCGTGGGCTTCCCCACCCTGACAAGTGTCAGGAGATGGAGACC
 SEQ ID NO:7     (631)    TTGCGAGGCGTGGGCTTCCCCACCCTGACAAGTGTCAGGAGATGGAGACC
 SEQ ID NO:1     (901)    TTGCGAGGCGTGGGCTTCCCCACCCTGACAAGTGTCAGGAGATGGAGACC
                          951                                               1000
SEQ ID NO:11       (1)    -------------------------------------------------G
SEQ ID NO:10      (81)    ATTTCCCATCTACTCTTGGGGTGTGTCTTGGCGAGGCAGGTTTGGGAGCG
 SEQ ID NO:9     (281)    ATTTCCCATCTACTCTTGGGGTGTGTCTTGGCGAGGCAGGTTTGGGAGCG
 SEQ ID NO:8     (481)    ATTTCCCATCTACTCTTGGGGTGTGTCTTGGCGAGGCAGGTTTGGGAGCG
 SEQ ID NO:7     (681)    ATTTCCCATCTACTCTTGGGGTGTGTCTTGGCGAGGCAGGTTTGGGAGCG
 SEQ ID NO:1     (951)    ATTTCCCATCTACTCTTGGGGTGTGTCTTGGCGAGGCAGGTTTGGGAGCG
                          1001                                              1050
SEQ ID NO:11       (2)    CTTGTGGGCGGCTTGGGGACACGTGGAGTGGGCTCCGAATGCGGATGCTA
SEQ ID NO:10     (131)    CTTGTGGGCGGCTTGGGGACACGTGGAGTGGGCTCCGAATGCGGATGCTA
 SEQ ID NO:9     (331)    CTTGTGGGCGGCTTGGGGACACGTGGAGTGGGCTCCGAATGCGGATGCTA
 SEQ ID NO:8     (531)    CTTGTGGGCGGCTTGGGGACACGTGGAGTGGGCTCCGAATGCGGATGCTA
 SEQ ID NO:7     (731)    CTTGTGGGCGGCTTGGGGACACGTGGAGTGGGCTCCGAATGCGGATGCTA
 SEQ ID NO:1    (1001)    CTTGTGGGCGGCTTGGGGACACGTGGAGTGGGCTCCGAATGCGGATGCTA
```

FIGURE 2 (Continued):

```
                            1051                                          1100
SEQ ID NO:11      (52)   CTCTGCGGGAATGGTGGTCTTCTCTTCCCTTACCACGGCGAGCCCGGAGG
SEQ ID NO:10     (181)   CTCTGCGGGAATGGTGGTCTTCTCTTCCCTTACCACGGCGAGCCCGGAGG
 SEQ ID NO:9     (381)   CTCTGCGGGAATGGTGGTCTTCTCTTCCCTTACCACGGCGAGCCCGGAGG
 SEQ ID NO:8     (581)   CTCTGCGGGAATGGTGGTCTTCTCTTCCCTTACCACGGCGAGCCCGGAGG
 SEQ ID NO:7     (781)   CTCTGCGGGAATGGTGGTCTTCTCTTCCCTTACCACGGCGAGCCCGGAGG
 SEQ ID NO:1    (1051)   CTCTGCGGGAATGGTGGTCTTCTCTTCCCTTACCACGGCGAGCCCGGAGG
                            1101                                          1150
SEQ ID NO:11     (102)   GACTTCCGGACGGGGATCATACTTGTTCTTTGGACCATTTGGTGCCATTG
SEQ ID NO:10     (231)   GACTTCCGGACGGGGATCATACTTGTTCTTTGGACCATTTGGTGCCATTG
 SEQ ID NO:9     (431)   GACTTCCGGACGGGGATCATACTTGTTCTTTGGACCATTTGGTGCCATTG
 SEQ ID NO:8     (631)   GACTTCCGGACGGGGATCATACTTGTTCTTTGGACCATTTGGTGCCATTG
 SEQ ID NO:7     (831)   GACTTCCGGACGGGGATCATACTTGTTCTTTGGACCATTTGGTGCCATTG
 SEQ ID NO:1    (1101)   GACTTCCGGACGGGGATCATACTTGTTCTTTGGACCATTTGGTGCCATTG
                            1151                                          1200
SEQ ID NO:11     (152)   GAATGATGTGGCCTTCCTTGCAGCTTGTCGTGCTTCGCCTCCAGGAGGAG
SEQ ID NO:10     (281)   GAATGATGTGGCCTTCCTTGCAGCTTGTCGTGCTTCGCCTCCAGGAGGAG
 SEQ ID NO:9     (481)   GAATGATGTGGCCTTCCTTGCAGCTTGTCGTGCTTCGCCTCCAGGAGGAG
 SEQ ID NO:8     (681)   GAATGATGTGGCCTTCCTTGCAGCTTGTCGTGCTTCGCCTCCAGGAGGAG
 SEQ ID NO:7     (881)   GAATGATGTGGCCTTCCTTGCAGCTTGTCGTGCTTCGCCTCCAGGAGGAG
 SEQ ID NO:1    (1151)   GAATGATGTGGCCTTCCTTGCAGCTTGTCGTGCTTCGCCTCCAGGAGGAG
                            1201                                          1250
SEQ ID NO:11     (202)   TTTGGTCGGTGGGCGCACGCCGGCCTCTTAGGGGTAGAGTGTCTATTCC
SEQ ID NO:10     (331)   TTTGGTCGGTGGGCGCACGCCGGCCTCTTAGGGGTAGAGTGTCTATTCC
 SEQ ID NO:9     (531)   TTTGGTCGGTGGGCGCACGCCGGCCTCTTAGGGGTAGAGTGTCTATTCC
 SEQ ID NO:8     (731)   TTTGGTCGGTGGGCGCACGCCGGCCTCTTAGGGGTAGAGTGTCTATTCC
 SEQ ID NO:7     (931)   TTTGGTCGGTGGGCGCACGCCGGCCTCTTAGGGGTAGAGTGTCTATTCC
 SEQ ID NO:1    (1201)   TTTGGTCGGTGGGCGCACGCCGGCCTCTTAGGGGTAGAGTGTCTATTCC
                            1251                                          1300
SEQ ID NO:11     (252)   AGCCTTGATGGTGAGTGGTTGGATAGCTAGCACATAGTCTTTTTTTCTCT
SEQ ID NO:10     (381)   AGCCTTGATGGTGAGTGGTTGGATAGCTAGCACATAGTCTTTTTTTCTCT
 SEQ ID NO:9     (581)   AGCCTTGATGGTGAGTGGTTGGATAGCTAGCACATAGTCTTTTTTTCTCT
 SEQ ID NO:8     (781)   AGCCTTGATGGTGAGTGGTTGGATAGCTAGCACATAGTCTTTTTTTCTCT
 SEQ ID NO:7     (981)   AGCCTTGATGGTGAGTGGTTGGATAGCTAGCACATAGTCTTTTTTTCTCT
 SEQ ID NO:1    (1251)   AGCCTTGATGGTGAGTGGTTGGATAGCTAGCACATAGTCTTTTTTTCTCT
                            1301                                          1350
SEQ ID NO:11     (302)   TTCTTGCCACTTGGTGATGTTGTATTGCCGCTTCGGCGTTGTACTAGCCT
SEQ ID NO:10     (431)   TTCTTGCCACTTGGTGATGTTGTATTGCCGCTTCGGCGTTGTACTAGCCT
 SEQ ID NO:9     (631)   TTCTTGCCACTTGGTGATGTTGTATTGCCGCTTCGGCGTTGTACTAGCCT
 SEQ ID NO:8     (831)   TTCTTGCCACTTGGTGATGTTGTATTGCCGCTTCGGCGTTGTACTAGCCT
 SEQ ID NO:7    (1031)   TTCTTGCCACTTGGTGATGTTGTATTGCCGCTTCGGCGTTGTACTAGCCT
 SEQ ID NO:1    (1301)   TTCTTGCCACTTGGTGATGTTGTATTGCCGCTTCGGCGTTGTACTAGCCT
                            1351                                          1400
SEQ ID NO:11     (352)   TCTGGCTCTTCTTATTTAATCGATGATGCACCCGCTGGGTGGCATTCTTG
SEQ ID NO:10     (481)   TCTGGCTCTTCTTATTTAATCGATGATGCACCCGCTGGGTGGCATTCTTG
 SEQ ID NO:9     (681)   TCTGGCTCTTCTTATTTAATCGATGATGCACCCGCTGGGTGGCATTCTTG
 SEQ ID NO:8     (881)   TCTGGCTCTTCTTATTTAATCGATGATGCACCCGCTGGGTGGCATTCTTG
 SEQ ID NO:7    (1081)   TCTGGCTCTTCTTATTTAATCGATGATGCACCCGCTGGGTGGCATTCTTG
 SEQ ID NO:1    (1351)   TCTGGCTCTTCTTATTTAATCGATGATGCACCCGCTGGGTGGCATTCTTG
```

FIGURE 2 (Continued):

```
                          1401                                              1450
SEQ ID NO:11     (402)    AAATTTTTTGAGAAAATACTCCTACAAAGGAAGTACAGTAATTTGATAC
SEQ ID NO:10     (531)    AAATTTTTTGAGAAAATACTCCTACAAAGGAAGTACAGTAATTTGATAC
 SEQ ID NO:9     (731)    AAATTTTTTGAGAAAATACTCCTACAAAGGAAGTACAGTAATTTGATAC
 SEQ ID NO:8     (931)    AAATTTTTTGAGAAAATACTCCTACAAAGGAAGTACAGTAATTTGATAC
 SEQ ID NO:7    (1131)    AAATTTTTTGAGAAAATACTCCTACAAAGGAAGTACAGTAATTTGATAC
 SEQ ID NO:1    (1401)    AAATTTTTTGAGAAAATACTCCTACAAAGGAAGTACAGTAATTTGATAC
                          1451                                              1500
SEQ ID NO:11     (452)    ACAATGCTTTCTCTAAATACGAAAATACAAACATCCTAATGTTATTCCAA
SEQ ID NO:10     (581)    ACAATGCTTTCTCTAAATACGAAAATACAAACATCCTAATGTTATTCCAA
 SEQ ID NO:9     (781)    ACAATGCTTTCTCTAAATACGAAAATACAAACATCCTAATGTTATTCCAA
 SEQ ID NO:8     (981)    ACAATGCTTTCTCTAAATACGAAAATACAAACATCCTAATGTTATTCCAA
 SEQ ID NO:7    (1181)    ACAATGCTTTCTCTAAATACGAAAATACAAACATCCTAATGTTATTCCAA
 SEQ ID NO:1    (1451)    ACAATGCTTTCTCTAAATACGAAAATACAAACATCCTAATGTTATTCCAA
                          1501                                              1550
SEQ ID NO:11     (502)    CTATGCTACTCCCTCCGTTCCTAAACTCTTATCTTTGTTTTTGTTCAAAT
SEQ ID NO:10     (631)    CTATGCTACTCCCTCCGTTCCTAAACTCTTATCTTTGTTTTTGTTCAAAT
 SEQ ID NO:9     (831)    CTATGCTACTCCCTCCGTTCCTAAACTCTTATCTTTGTTTTTGTTCAAAT
 SEQ ID NO:8    (1031)    CTATGCTACTCCCTCCGTTCCTAAACTCTTATCTTTGTTTTTGTTCAAAT
 SEQ ID NO:7    (1231)    CTATGCTACTCCCTCCGTTCCTAAACTCTTATCTTTGTTTTTGTTCAAAT
 SEQ ID NO:1    (1501)    CTATGCTACTCCCTCCGTTCCTAAACTCTTATCTTTGTTTTTGTTCAAAT
                          1551                                              1600
SEQ ID NO:11     (552)    TTGTACCAAACAACGACAAAAATTTAGTAACGGAGGAAGTATATATACGA
SEQ ID NO:10     (681)    TTGTACCAAACAACGACAAAAATTTAGTAACGGAGGAAGTATATATACGA
 SEQ ID NO:9     (881)    TTGTACCAAACAACGACAAAAATTTAGTAACGGAGGAAGTATATATACGA
 SEQ ID NO:8    (1081)    TTGTACCAAACAACGACAAAAATTTAGTAACGGAGGAAGTATATATACGA
 SEQ ID NO:7    (1281)    TTGTACCAAACAACGACAAAAATTTAGTAACGGAGGAAGTATATATACGA
 SEQ ID NO:1    (1551)    TTGTACCAAACAACGACAAAAATTTAGTAACGGAGGAAGTATATATACGA
                          1601                                              1650
SEQ ID NO:11     (602)    AGTGATACCAAATAAGGTGTTTCTTTACTTGAAAGCTAGTTCCTCTGAGG
SEQ ID NO:10     (731)    AGTGATACCAAATAAGGTGTTTCTTTACTTGAAAGCTAGTTCCTCTGAGG
 SEQ ID NO:9     (931)    AGTGATACCAAATAAGGTGTTTCTTTACTTGAAAGCTAGTTCCTCTGAGG
 SEQ ID NO:8    (1131)    AGTGATACCAAATAAGGTGTTTCTTTACTTGAAAGCTAGTTCCTCTGAGG
 SEQ ID NO:7    (1331)    AGTGATACCAAATAAGGTGTTTCTTTACTTGAAAGCTAGTTCCTCTGAGG
 SEQ ID NO:1    (1601)    AGTGATACCAAATAAGGTGTTTCTTTACTTGAAAGCTAGTTCCTCTGAGG
                          1651                                              1700
SEQ ID NO:11     (652)    TAAAAGAAATGATGAGGATCAAGGAAGGCCCATTTCTTGCCGGCACGCAG
SEQ ID NO:10     (781)    TAAAAGAAATGATGAGGATCAAGGAAGGCCCATTTCTTGCCGGCACGCAG
 SEQ ID NO:9     (981)    TAAAAGAAATGATGAGGATCAAGGAAGGCCCATTTCTTGCCGGCACGCAG
 SEQ ID NO:8    (1181)    TAAAAGAAATGATGAGGATCAAGGAAGGCCCATTTCTTGCCGGCACGCAG
 SEQ ID NO:7    (1381)    TAAAAGAAATGATGAGGATCAAGGAAGGCCCATTTCTTGCCGGCACGCAG
 SEQ ID NO:1    (1651)    TAAAAGAAATGATGAGGATCAAGGAAGGCCCATTTCTTGCCGGCACGCAG
                          1701                                              1750
SEQ ID NO:11     (702)    TTGCCGAAGTCAGTAGATTTAAAATGACCTCACATACTGAAGAAGGAAAG
SEQ ID NO:10     (831)    TTGCCGAAGTCAGTAGATTTAAAATGACCTCACATACTGAAGAAGGAAAG
 SEQ ID NO:9    (1031)    TTGCCGAAGTCAGTAGATTTAAAATGACCTCACATACTGAAGAAGGAAAG
 SEQ ID NO:8    (1231)    TTGCCGAAGTCAGTAGATTTAAAATGACCTCACATACTGAAGAAGGAAAG
 SEQ ID NO:7    (1431)    TTGCCGAAGTCAGTAGATTTAAAATGACCTCACATACTGAAGAAGGAAAG
 SEQ ID NO:1    (1701)    TTGCCGAAGTCAGTAGATTTAAAATGACCTCACATACTGAAGAAGGAAAG
```

FIGURE 2 (Continued):

```
                         1751                                              1800
SEQ ID NO:11    (752)    GGAAGTTAACCACGCCATTGTTGCTTTAGCAGAAAGCAACCATATCCTAA
SEQ ID NO:10    (881)    GGAAGTTAACCACGCCATTGTTGCTTTAGCAGAAAGCAACCATATCCTAA
SEQ ID NO:9    (1081)    GGAAGTTAACCACGCCATTGTTGCTTTAGCAGAAAGCAACCATATCCTAA
SEQ ID NO:8    (1281)    GGAAGTTAACCACGCCATTGTTGCTTTAGCAGAAAGCAACCATATCCTAA
SEQ ID NO:7    (1481)    GGAAGTTAACCACGCCATTGTTGCTTTAGCAGAAAGCAACCATATCCTAA
SEQ ID NO:1    (1751)    GGAAGTTAACCACGCCATTGTTGCTTTAGCAGAAAGCAACCATATCCTAA
                         1801                                              1850
SEQ ID NO:11    (802)    TTAACATCACAGTACACGTTGAAACGGCAGGGCACGATAATTGGTGAAGA
SEQ ID NO:10    (931)    TTAACATCACAGTACACGTTGAAACGGCAGGGCACGATAATTGGTGAAGA
SEQ ID NO:9    (1131)    TTAACATCACAGTACACGTTGAAACGGCAGGGCACGATAATTGGTGAAGA
SEQ ID NO:8    (1331)    TTAACATCACAGTACACGTTGAAACGGCAGGGCACGATAATTGGTGAAGA
SEQ ID NO:7    (1531)    TTAACATCACAGTACACGTTGAAACGGCAGGGCACGATAATTGGTGAAGA
SEQ ID NO:1    (1801)    TTAACATCACAGTACACGTTGAAACGGCAGGGCACGATAATTGGTGAAGA
                         1851                                              1900
SEQ ID NO:11    (852)    CTGATTCCAGGGAGCATCGTGGCACGCAAAAACGCCCTTGCCTTGTTCCC
SEQ ID NO:10    (981)    CTGATTCCAGGGAGCATCGTGGCACGCAAAAACGCCCTTGCCTTGTTCCC
SEQ ID NO:9    (1181)    CTGATTCCAGGGAGCATCGTGGCACGCAAAAACGCCCTTGCCTTGTTCCC
SEQ ID NO:8    (1381)    CTGATTCCAGGGAGCATCGTGGCACGCAAAAACGCCCTTGCCTTGTTCCC
SEQ ID NO:7    (1581)    CTGATTCCAGGGAGCATCGTGGCACGCAAAAACGCCCTTGCCTTGTTCCC
SEQ ID NO:1    (1851)    CTGATTCCAGGGAGCATCGTGGCACGCAAAAACGCCCTTGCCTTGTTCCC
                         1901                                              1950
SEQ ID NO:11    (902)    TTATAAATAGTGGTGCAGAAGATACATTTGTGATCACCATCTCAAAGCGC
SEQ ID NO:10   (1031)    TTATAAATAGTGGTGCAGAAGATACATTTGTGATCACCATCTCAAAGCGC
SEQ ID NO:9    (1231)    TTATAAATAGTGGTGCAGAAGATACATTTGTGATCACCATCTCAAAGCGC
SEQ ID NO:8    (1431)    TTATAAATAGTGGTGCAGAAGATACATTTGTGATCACCATCTCAAAGCGC
SEQ ID NO:7    (1631)    TTATAAATAGTGGTGCAGAAGATACATTTGTGATCACCATCTCAAAGCGC
SEQ ID NO:1    (1901)    TTATAAATAGTGGTGCAGAAGATACATTTGTGATCACCATCTCAAAGCGC
                         1951                                              2000
SEQ ID NO:11    (952)    CTCTTTATTCCCCTTTCATCTTGAGCTTAAGTACTAGAGAAAAATTAAGG
SEQ ID NO:10   (1081)    CTCTTTATTCCCCTTTCATCTTGAGCTTAAGTACTAGAGAAAAATTAAGG
SEQ ID NO:9    (1281)    CTCTTTATTCCCCTTTCATCTTGAGCTTAAGTACTAGAGAAAAATTAAGG
SEQ ID NO:8    (1481)    CTCTTTATTCCCCTTTCATCTTGAGCTTAAGTACTAGAGAAAAATTAAGG
SEQ ID NO:7    (1681)    CTCTTTATTCCCCTTTCATCTTGAGCTTAAGTACTAGAGAAAAATTAAGG
SEQ ID NO:1    (1951)    CTCTTTATTCCCCTTTCATCTTGAGCTTAAGTACTAGAGAAAAATTAAGG
```

FIGURE 3:

```
                        1                                                  50
SEQ ID NO:12    (1)    TTTCGTGTGCTTACTTGGGGCTTCCTTTGGGCCTGCGGAAGCAGACGGCG
SEQ ID NO:1     (1)    TTTCGTGTGCTTACTTGGGGCTTCCTTTGGGCCTGCGGAAGCAGACGGCG
                        51                                                 100
SEQ ID NO:12    (51)   TGCCAGGTACGAGGTTGTTGGTGGACAATGTGGATGGACGATTTCTAGCT
SEQ ID NO:1     (51)   TGCCAGCT--GAGACCGTTGGTGGACAATGTGGATGGACG---TCTAGCT
                        101                                                150
SEQ ID NO:12    (101)  TCGTGGAAGGCCCTTCTCCTT----AAGGGAGGATGACTGGTGCTGGTCAA
SEQ ID NO:1     (96)   TCGTGGAAGGCCCTTCTCCTTTCCAAGGGAGGATGACTGGTGCTGGTCAA
                        151                                                200
SEQ ID NO:12    (148)  GTCCACCCTGACAGCGATGCCGGTCTACTCGATGATGTCACTCGACCTTT
SEQ ID NO:1     (146)  GTCCACCCTGACAGCGATGCCGGTCTACTCGATGATGTCACTCGACCTTT
                        201                                                250
SEQ ID NO:12    (198)  CGGACAAGATCATCAAAGGGGTGGACAAGGTATGTCGTGGTTTCCTTTGG
SEQ ID NO:1     (196)  CGGACAAGATCATCAAAGGGGTGGACAAGATCTGTCGTGGTTTCCTTTGG
                        251                                                300
SEQ ID NO:12    (248)  CGTGGTCAGAAGGACGCTAAAGGGGGGGGGGCATTGTATGGTGGCTTGGG
SEQ ID NO:1     (246)  CGTGGTCAGAAGGACGCTAAAGGGGGGGGGGCATTGTATGGTGGCTTGGG
                        301                                                350
SEQ ID NO:12    (298)  TCGTGGTGTGTTCGCCGACCGCTTTCGGTGGACTCGGCGTTTCCAAATCT
SEQ ID NO:1     (296)  TCGTGGTGTGTTCGCCGAAGCCTTTCGGTGGACTCGGAATT-CCAAATCT
                        351                                                400
SEQ ID NO:12    (348)  TCGCATCCTC---CCAG-CCTTGAGGGTCCGCTAGAGGTGGCTTGAGAGGG
SEQ ID NO:1     (345)  TCGCATGCTCAACGAGGCCTTGAGGGTCCGCTAGAGGTGGCTTGAGAGGG
                        401                                                450
SEQ ID NO:12    (395)  TGGACGATTCCAAACCCGATGGTCGGTTTCAAGGTTGAGACGCCCAGAGG
SEQ ID NO:1     (395)  TGGACGATTCCAAACCATG-GGTCGGTTTCAAGGTTGAGACGCCCAGAGG
                        451                                                500
SEQ ID NO:12    (445)  TCTATGTTATCTTTGAGGCGGCCACTTCCTCTTTGGTGGGCGATGGCCGG
SEQ ID NO:1     (444)  TCTATGTTATCTTTGAGGCGGCCACTTCCTCTTTGGTGGGCGATGGCCGG
                        501                                                550
SEQ ID NO:12    (495)  ACGTTTCCCTCTTCTGGACCGATTGTTGGCTGCATGGCGTCTGTTTTCGA
SEQ ID NO:1     (494)  AAGA---CCCTCTTCTGGACCGATCGTTGGCTGCATGGCGTCTGTTTTCGA
                        551                                                600
SEQ ID NO:12    (545)  GATGCGTTCCTGATCCTCGTGGGCCATGTTTGCCACAAGTTTTTGCTTAC
SEQ ID NO:1     (542)  GATGCGTTCCTGATCCTCGTGGGCCATGTTTGCCACAAGTTTTTGCGCAC
                        601                                                650
SEQ ID NO:12    (595)  GCGCACAGTGCGGGAGGCTCTGCATGGAGCGTGGACTGGCGACATGGGTC
SEQ ID NO:1     (592)  GCGCACAGTGCGGGAGGCTCTGCATGGAGCGTGGACTGGCGACATGGGTC
                        651                                                700
SEQ ID NO:12    (645)  CAGACCTAAAGGGAAGCTACTCTTGAGGACTTC---ACTCTCTGGGACTG
SEQ ID NO:1     (642)  CAGACCTAAAGGGAAGCTACTCTTGAGGAGTTCCTCACTCTCTGGGACTG
                        701                                                750
SEQ ID NO:12    (692)  GCTTCGTGGGGTCCAACTGGAAGAAGGGAGGGCCGACTCTCTTCATTGGA
SEQ ID NO:1     (692)  GCTTCGTGGGGTCCAACTGGAAGAAGGGAGGGCCGACTCTCTTCATTGGA
                        751                                                800
SEQ ID NO:12    (742)  ACTGGTGTGGTGGTGATAGTTACTCGGCAAAGACTGCTTATGCGAATCT-
SEQ ID NO:1     (742)  ACTGGTCTCGTGGTGATAGTTACTCGGCAAAGACTGCTTATGCGAATCTC
                        801                                                850
SEQ ID NO:12    (791)  -TCACTGGCCGCATGGTTGACCCGTTAGCGGCTGAGAGTTAGGGCTTCGG
SEQ ID NO:1     (792)  TTCACTGGCCGCATGGTTGACCCGTTAGCGGCTGAGATCTAGGGCTTCGG
                        851                                                900
SEQ ID NO:12    (840)  AGAGGTGTCGTTTCTTCGTCTGGCTCGCAGTTCTTGAAATAGATGCTAGA
SEQ ID NO:1     (842)  AGAGGTGTCGTTTCTTCGTCTGGCTCGCAGTTC----GAAATAGATGCTAGA
```

FIGURE 3 (Continued):

```
                           901                                              950
SEQ ID NO:12   (890)   CGGCGGATCGCTTGCGAGGCGTGGGCTTCCCCACCCTGACAAGTGTCAGG
SEQ ID NO:1    (890)   CGGCGGATCGCTTGCGAGGCGTGGGCTTCCCCACCCTGACAAGTGTCAGG
                           951                                             1000
SEQ ID NO:12   (940)   AGATGGAGTCGATTTCCCATCTACTCTTGGGGTGTGTCTTGGCGAGGCAG
SEQ ID NO:1    (940)   AGATGGAGACCATTTCCCATCTACTCTTGGGGTGTGTCTTGGCGAGGCAG
                          1001                                             1050
SEQ ID NO:12   (990)   GTTTGGGAGCGCTTGTGGGCGGCTTGGGGACACGTGGAGTGGGCTCCGAA
SEQ ID NO:1    (990)   GTTTGGGAGCGCTTGTGGGCGGCTTGGGGACACGTGGAGTGGGCTCCGAA
                          1051                                             1100
SEQ ID NO:12  (1040)   TGCGGATGCTACTCTGCGGGAATGGTGGTCTTTCTCTTCCCTTACCACGG
SEQ ID NO:1   (1040)   TGCGGATGCTACTCTGCGGGAATGGTGGTCTT-CTCTTCCCTTACCACGG
                          1101                                             1150
SEQ ID NO:12  (1090)   CGAGCCCGGAGGGACTTCCGGACGGGATCATACTTGTTCTTTGGACCAT
SEQ ID NO:1   (1089)   CGAGCCCGGAGGGACTTCCGGACGGGATCATACTTGTTCTTTGGACCAT
                          1151                                             1200
SEQ ID NO:12  (1140)   TTGGTGCCATTGGAATGATGTGGCCTTCCTTGCAGCTTGTCGTGCTTCGC
SEQ ID NO:1   (1139)   TTGGTGCCATTGGAATGATGTGGCCTTCCTTGCAGCTTGTCGTGCTTCGC
                          1201                                             1250
SEQ ID NO:12  (1190)   CTGGAGGAATTGTTTGGTCGGTGGGCGCACGCCGGCCTCTTTAGGGGTAG
SEQ ID NO:1   (1189)   CTCCAGGAGGAGTTTGGTCGGTGGGCGCACGCCGGCCTCTTTAGGGGTAG
                          1251                                             1300
SEQ ID NO:12  (1240)   AGTGTCTATTCCAGCCTTGATGGTGAGTGGTTGGATAGCTAGCACATAGT
SEQ ID NO:1   (1239)   AGTGTCTATTCCAGCCTTGATGGTGAGTGGTTGGATAGCTAGCACATAGT
                          1301                                             1350
SEQ ID NO:12  (1290)   CTTTTTTTCTCTTTCTTGCCACTTGGTGATGTTGTATTGCCGCTTCGGCG
SEQ ID NO:1   (1289)   CTTTTTTTCTCTTTCTTGCCACTTGGTGATGTTGTATTGCCGCTTCGGCG
                          1351                                             1400
SEQ ID NO:12  (1340)   TTGTACTAGCCTTCTGGCTCTTCTTATTTAAT-GATGATGCACCCGCTGG
SEQ ID NO:1   (1339)   TTGTACTAGCCTTCTGGCTCTTCTTATTTAATCGATGATGCACCCGCTGG
                          1401                                             1450
SEQ ID NO:12  (1389)   GTGGCATTCTTGAAATTTTTTTGAGAAAATACTCCTACAAAGGAAGTACA
SEQ ID NO:1   (1389)   GTGGCATTCTTGAAATTTTTTTGAGAAAATACTCCTACAAAGGAAGTACA
                          1451                                             1500
SEQ ID NO:12  (1439)   GTAATTTGATACACAATGCTTTCTCTAAATACGAAAATACAAACATCCTA
SEQ ID NO:1   (1439)   GTAATTTGATACACAATGCTTTCTCTAAATACGAAAATACAAACATCCTA
                          1501                                             1550
SEQ ID NO:12  (1489)   ATGTTATTCCAACTATGCTACTCCCTCCGTTCCTAAACTCTTATCTTTGT
SEQ ID NO:1   (1489)   ATGTTATTCCAACTATGCTACTCCCTCCGTTCCTAAACTCTTATCTTTGT
                          1551                                             1600
SEQ ID NO:12  (1539)   TTTTGTTCAAATTTGTACCAAACAACGACAAAAATTTAGTAACGGAGGAA
SEQ ID NO:1   (1539)   TTTTGTTCAAATTTGTACCAAACAACGACAAAAATTTAGTAACGGAGGAA
                          1601                                             1650
SEQ ID NO:12  (1589)   GTATATATACGAAGTGATACCAAATAAGGTGTTTCTTTACTTGAAAGCTA
SEQ ID NO:1   (1589)   GTATATATACGAAGTGATACCAAATAAGGTGTTTCTTTACTTGAAAGCTA
                          1651                                             1700
SEQ ID NO:12  (1639)   GTTCCTCTGAGGTAAAAGAAATGATGAGGATCAAGGAAGGCCCATTTCTT
SEQ ID NO:1   (1639)   GTTCCTCTGAGGTAAAAGAAATGATGAGGATCAAGGAAGGCCCATTTCTT
                          1701                                             1750
SEQ ID NO:12  (1689)   GCCGGCACGCAGTTGCCGAAGTCAGTAGATTTAAAATGACCTCACATACT
SEQ ID NO:1   (1689)   GCCGGCACGCAGTTGCCGAAGTCAGTAGATTTAAAATGACCTCACATACT
                          1751                                             1800
SEQ ID NO:12  (1739)   GAAGAAGGAAAGGGAAGTTAACCACGCCATTGTTGCTTTAGCAGAAAGCA
SEQ ID NO:1   (1739)   GAAGAAGGAAAGGGAAGTTAACCACGCCATTGTTGCTTTAGCAGAAAGCA
```

FIGURE 3 (Continued):

```
                         1801                                              1850
SEQ ID NO:12   (1789)    ACCATATCCTAATTAACATCACAGTACACGTTGAAACGGCAGGGCACGAT
 SEQ ID NO:1   (1789)    ACCATATCCTAATTAACATCACAGTACACGTTGAAACGGCAGGGCACGAT
                         1851                                              1900
SEQ ID NO:12   (1839)    AATTGGTGAAGACTGATTCCAGGGAGCATCGTGGCACGCAAAAACGCCCT
 SEQ ID NO:1   (1839)    AATTGGTGAAGACTGATTCCAGGGAGCATCGTGGCACGCAAAAACGCCCT
                         1901                                              1950
SEQ ID NO:12   (1889)    TGCCTTGTTCCCTTATAAATAGTGGTGCAGAAGATACATTTGTGATCACC
 SEQ ID NO:1   (1889)    TGCCTTGTTCCCTTATAAATAGTGGTGCAGAAGATACATTTGTGATCACC
                         1951                                              2000
SEQ ID NO:12   (1939)    ATCTCAAAGCGCCTCTTTATTCCCCTTTCATCTTGAGCTTAAGTACTAGA
 SEQ ID NO:1   (1939)    ATCTCAAAGCGCCTCTTTATTCCCCTTTCATCTTGAGCTTAAGTACTAGA
                         2001      2012
SEQ ID NO:12   (1989)    GAAAAATTAAGG
 SEQ ID NO:1   (1989)    GAAAAATTAAGG
```

FIGURE 4:

```
                            1                                                  50
SEQ ID NO:16      (1)   GATGCACGCGACGCGCTGCTGCTTGTGGTGTGTGTTTGTGTGATCTCGAC
SEQ ID NO:15      (1)   GATGCACGCGACGCGCTGCTGCTTGTGGTGTGTGTTTGTGTGATCTCGAC
SEQ ID NO:14      (1)   GATGCACGCGACGCGCTGCTGCTTGTGGTGTGTGTTTGTGTGATCTCGAC
SEQ ID NO:13      (1)   GATGCACGCGACGCGCTGCTGCTTGTGGTGTGTGTTTGTGTGATCTCGAC
 SEQ ID NO:3      (1)   GATGCACGCGACGCGCTGCTGCTTGTGGTGTGTGTTTGTGTGATCTCGAC
                           51                                                 100
SEQ ID NO:16     (51)   TGAATAAAAGGGACACGGTACATCCGGGGTTGGTTGGTGCTCGAGTCGAG
SEQ ID NO:15     (51)   TGAATAAAAGGGACACGGTACATCCGGGGTTGGTTGGTGCTCGAGTCGAG
SEQ ID NO:14     (51)   TGAATAAAAGGGACACGGTACATCCGGGGTTGGTTGGTGCTCGAGTCGAG
SEQ ID NO:13     (51)   TGAATAAAAGGGACACGGTACATCCGGGGTTGGTTGGTGCTCGAGTCGAG
 SEQ ID NO:3     (51)   TGAATAAAAGGGACACGGTACATCCGGGGTTGGTTGGTGCTCGAGTCGAG
                          101                                                 150
SEQ ID NO:16    (101)   TGTGCAAGGTTGTGTGGTTTGCCAGCTCTTGGTGTGTGTCTCCTTGTGCT
SEQ ID NO:15    (101)   TGTGCAAGGTTGTGTGGTTTGCCAGCTCTTGGTGTGTGTCTCCTTGTGCT
SEQ ID NO:14    (101)   TGTGCAAGGTTGTGTGGTTTGCCAGCTCTTGGTGTGTGTCTCCTTGTGCT
SEQ ID NO:13    (101)   TGTGCAAGGTTGTGTGGTTTGCCAGCTCTTGGTGTGTGTCTCCTTGTGCT
 SEQ ID NO:3    (101)   TGTGCAAGGTTGTGTGGTTTGCCAGCTCTTGGTGTGTGTCTCCTTGTGCT
                          151                                                 200
SEQ ID NO:16    (151)   CATGTGACTTGTGAAACCATTAATAGTAACCACTTTGTGCTTGTGTGTGT
SEQ ID NO:15    (151)   CATGTGACTTGTGAAACCATTAATAGTAACCACTTTGTGCTTGTGTGTGT
SEQ ID NO:14    (151)   CATGTGACTTGTGAAACCATTAATAGTAACCACTTTGTGCTTGTGTGTGT
SEQ ID NO:13    (151)   CATGTGACTTGTGAAACCATTAATAGTAACCACTTTGTGCTTGTGTGTGT
 SEQ ID NO:3    (151)   CATGTGACTTGTGAAACCATTAATAGTAACCACTTTGTGCTTGTGTGTGT
                          201                                                 250
SEQ ID NO:16    (201)   GTGGGCACCTGTGTTTCTGTAATGGTCTATCTGGAGTGAATATATACAAG
SEQ ID NO:15    (201)   GTGGGCACCTGTGTTTCTGTAATGGTCTATCTGGAGTGAATATATACAAG
SEQ ID NO:14    (201)   GTGGGCACCTGTGTTTCTGTAATGGTCTATCTGGAGTGAATATATACAAG
SEQ ID NO:13    (201)   GTGGGCACCTGTGTTTCTGTAATGGTCTATCTGGAGTGAATATATACAAG
 SEQ ID NO:3    (201)   GTGGGCACCTGTGTTTCTGTAATGGTCTATCTGGAGTGAATATATACAAG
                          251                                                 300
SEQ ID NO:16    (251)   ACAGGTTTGCCTAACCATGCCTTTTCCTTCCTTGAGGTCATCGCGCCAAC
SEQ ID NO:15    (251)   ACAGGTTTGCCTAACCATGCCTTTTCCTTCCTTGAGGTCATCGCGCCAAC
SEQ ID NO:14    (251)   ACAGGTTTGCCTAACCATGCCTTTTCCTTCCTTGAGGTCATCGCGCCAAC
SEQ ID NO:13    (251)   ACAGGTTTGCCTAA------------------------------------
 SEQ ID NO:3    (251)   ACAGGTTTGCCTAACCATGCCTTTTCCTTCCTTGAGGTCATCGCGCCAAC
                          301                                                 350
SEQ ID NO:16    (301)   ACGAATGACGAGAACCAATGATCTTAGGACTATCAAATAGACAATATAAC
SEQ ID NO:15    (301)   ACGAATGACGAGAACCAATGATCTTAGGACTATCAAATAGACAATATAAC
SEQ ID NO:14    (301)   ACGAATGACGAGAACCAATGATCTTAGGACTA------------------
SEQ ID NO:13    (265)   --------------------------------------------------
 SEQ ID NO:3    (301)   ACGAATGACGAGAACCAATGATCTTAGGACTATCAAATAGACAATATAAC
                          351                                                 400
SEQ ID NO:16    (351)   TCAGCATGGAGCAATGTACTGCTAATGAACGGTCCTAATCAATACAGTTG
SEQ ID NO:15    (351)   TCAGCATGGAGCAATGTACTGCTAATGAACGGTCCTAATCAATACAGTTG
SEQ ID NO:14    (333)   --------------------------------------------------
SEQ ID NO:13    (265)   --------------------------------------------------
 SEQ ID NO:3    (351)   TCAGCATGGAGCAATGTACTGCTAATGAACGGTCCTAATCAATACAGTTG
                          401                                                 450
SEQ ID NO:16    (401)   GGAAGCAGTAATCGATGGAAAACACTTCCTCAGTTCAGAAGGGAACATGT
SEQ ID NO:15    (401)   GGAAGCAGTAATCGATGGAAAACACTTCCTCAGTTCAGAAGGGAACATGT
SEQ ID NO:14    (333)   --------------------------------------------------
SEQ ID NO:13    (265)   --------------------------------------------------
 SEQ ID NO:3    (401)   GGAAGCAGTAATCGATGGAAAACACTTCCTCAGTTCAGAAGGGAACATGT
```

FIGURE 4 (Continued):

```
                        451                                              500
SEQ ID NO:16    (451)   AGATGGGAAAGTAAACAGGATATATAGACACATGCAGTTAGGTCTACCAC
SEQ ID NO:15    (451)   AGATGGGAAAGTAAACAGGATATATAGACACATGCAGTTAGGTCTACCAC
SEQ ID NO:14    (333)   --------------------------------------------------
SEQ ID NO:13    (265)   --------------------------------------------------
 SEQ ID NO:3    (451)   AGATGGGAAAGTAAACAGGATATATAGACACATGCAGTTAGGTCTACCAC
                        501                                              550
SEQ ID NO:16    (501)   AAGAAGACATGCCACAGGACTAAAAACAGAAGCTGGGTTTGGAACAACTT
SEQ ID NO:15    (501)   AAGAAGACATGCCACAGGACTAAAAACAGAAGCTGGGTTTGGAACAACTT
SEQ ID NO:14    (333)   --------------------------------------------------
SEQ ID NO:13    (265)   --------------------------------------------------
 SEQ ID NO:3    (501)   AAGAAGACATGCCACAGGACTAAAAACAGAAGCTGGGTTTGGAACAACTT
                        551                                              600
SEQ ID NO:16    (551)   ATGCAGACGCTAGCTATCCAGATAAACCTTAGAGAAACAGCTATGAGAAT
SEQ ID NO:15    (551)   ATGCAGACGCTAGCTATCCAGATAAACCTTAGAGAAACAGCTATGAGAAT
SEQ ID NO:14    (333)   --------------------------------------------------
SEQ ID NO:13    (265)   --------------------------------------------------
 SEQ ID NO:3    (551)   ATGCAGACGCTAGCTATCCAGATAAACCTTAGAGAAACAGCTATGAGAAT
                        601                                              650
SEQ ID NO:16    (601)   AAGCGTCTGAAATTTGTAGTTGCCTGTTTGGAATGGCTTATGGACGACAA
SEQ ID NO:15    (601)   AAGCGTCTGAAATTTGTAGTTGCCTGTTTG--------------------
SEQ ID NO:14    (333)   --------------------------------------------------
SEQ ID NO:13    (265)   --------------------------------------------------
 SEQ ID NO:3    (601)   AAGCGTCTGAAATTTGTAGTTGCCTGTTTGGAATGGCTTATGGACGACAA
                        651                                              700
SEQ ID NO:16    (651)   GCTTATTTTCTGGAGTAGCCTACAAGTACAAGCCAAGGCACATGCTGTTC
SEQ ID NO:15    (631)   --------------------------------------------------
SEQ ID NO:14    (333)   --------------------------------------------------
SEQ ID NO:13    (265)   --------------------------------------------------
 SEQ ID NO:3    (651)   GCTTATTTTCTGGAGTAGCCTACAAGTACAAGCCAAGGCACATGCTGTTC
                        701                                              750
SEQ ID NO:16    (701)   CAAACTGGCCCATATTTTGCACAACCA-----------------------
SEQ ID NO:15    (631)   --------------------------------------------------
SEQ ID NO:14    (333)   --------------------------------------------------
SEQ ID NO:13    (265)   --------------------------------------------------
 SEQ ID NO:3    (701)   CAAACTGGCCCATATTTTGCACAACCAAAGGAAAAGAGACAGTGACATAA
                        751                                              800
SEQ ID NO:16    (728)   --------------------------------------------------
SEQ ID NO:15    (631)   --------------------------------------------------
SEQ ID NO:14    (333)   --------------------------------------------------
SEQ ID NO:13    (265)   --------------------------------------------------
 SEQ ID NO:3    (751)   GAGCATCTCCAGTGATTCAGTGAGATACCCCAAAGTCATCCAAATGTCCG
                        801                                              850
SEQ ID NO:16    (728)   --------------------------------------------------
SEQ ID NO:15    (631)   --------------------------------------------------
SEQ ID NO:14    (333)   --------------------------------------------------
SEQ ID NO:13    (265)   --------------------------------------------------
 SEQ ID NO:3    (801)   TTTCGGCCGAAATGGACATGCTGGCCAGAAAAACATCTCCCAATGGGTTA
                        851                                              900
SEQ ID NO:16    (728)   --------------------------------------------------
SEQ ID NO:15    (631)   --------------------------------------------------
SEQ ID NO:14    (333)   --------------------------------------------------
SEQ ID NO:13    (265)   --------------------------------------------------
 SEQ ID NO:3    (851)   CCCCAAATAGATATTTTGTATGTTTTGTCCGGCCCAATCCCCAAACATCT
```

FIGURE 4 (Continued):

```
                         901                                              950
SEQ ID NO:16    (728)    --------------------------------------------------
SEQ ID NO:15    (631)    --------------------------------------------------
SEQ ID NO:14    (333)    --------------------------------------------------
SEQ ID NO:13    (265)    --------------------------------------------------
 SEQ ID NO:3    (901)    CCTAAATTTGGGGCAACTTTGCGGTGTCCAGTGTCCGGTGTCCGGGCCCA
                         951                                              1000
SEQ ID NO:16    (728)    --------------------------------------------------
SEQ ID NO:15    (631)    --------------------------------------------------
SEQ ID NO:14    (333)    --------------------------------------------------
SEQ ID NO:13    (265)    --------------------------------------------------
 SEQ ID NO:3    (951)    CTTCTTTTTCTCCCAAGCGAGCATCTTCCTCCCGAAGCACGAAGCCCCG
                         1001
SEQ ID NO:16    (728)    --
SEQ ID NO:15    (631)    --
SEQ ID NO:14    (333)    --
SEQ ID NO:13    (265)    --
 SEQ ID NO:3   (1001)    TC
```

FIGURE 5:

```
                              1                                                  50
SEQ ID NO:18     (1)   GATGCACGCGACGCGCTGCTGCTTGTGGTGTGTGTTTGTGTGATCTCGAC
SEQ ID NO:17     (1)   GATGCACGCGACGCGCTGCTGCTTGTGGTGTGTGTTTGTGTGATCTCGAC
SEQ ID NO:3      (1)   GATGCACGCGACGCGCTGCTGCTTGTGGTGTGTGTTTGTGTGATCTCGAC
                              51                                                 100
SEQ ID NO:18     (51)  TGAATAAAAGGGACACGGTACATCCGGGGTTGGTTGGTGCTCGAAGTTGG
SEQ ID NO:17     (51)  TGAATAAAAGGGACACGGTACATCCGGGGTTGGTTGGTGCTCGAGTCGAG
SEQ ID NO:3      (51)  TGAATAAAAGGGACACGGTACATCCGGGGTTGGTTGGTGCTCGAGTCGAG
                              101                                                150
SEQ ID NO:18     (101) TGTGCAAGGTTGTGTGGTTTGCCAGCTCTTGGTGTGTGTCTCCTTGTGCT
SEQ ID NO:17     (101) TGTGCAAGGTTGTGTGGTTTGCCAGCTCTTGGTGTGTGTCTCCTTGTGCT
SEQ ID NO:3      (101) TGTGCAAGGTTGTGTGGTTTGCCAGCTCTTGGTGTGTGTCTCCTTGTGCT
                              151                                                200
SEQ ID NO:18     (151) CATGTGACTTGTGAAACCATTAATAGTAACCACTTTGTGCTTGTGTGTGT
SEQ ID NO:17     (151) CATGTGACTTGTGAAACCATTAATAGTAACCACTTTGTGCTTGTGTGTGT
SEQ ID NO:3      (151) CATGTGACTTGTGAAACCATTAATAGTAACCACTTTGTGCTTGTGTGTGT
                              201                                                250
SEQ ID NO:18     (201) GTGGGCACCTGTGTTTCTGTAATGGTCTATCTGGAGTGAATATATACAAG
SEQ ID NO:17     (201) GTGGGCACCTGTGTTTCTGTAATGGTCTATCTGGAGTGAATATATACAAG
SEQ ID NO:3      (201) GTGGGCACCTGTGTTTCTGTAATGGTCTATCTGGAGTGAATATATACAAG
                              251                                                300
SEQ ID NO:18     (251) ACAGGTTTGCCTAACCATGCCTTTTCCTTCCTTGAGGTCATCGCGCCAAC
SEQ ID NO:17     (251) ACAGGTTTGCCTAACCATGCCTTTTCCTTCCTTGAGGTCATCGCGCCAAC
SEQ ID NO:3      (251) ACAGGTTTGCCTAACCATGCCTTTTCCTTCCTTGAGGTCATCGCGCCAAC
                              301                                                350
SEQ ID NO:18     (301) ACGAATGACGAGAACCAATGATCTTAGGACTATCAAATAGACAATATAAC
SEQ ID NO:17     (301) ACGAATGACGAGAACCAATGATCTTAGGACTATCAAATAGACAATATAAC
SEQ ID NO:3      (301) ACGAATGACGAGAACCAATGATCTTAGGACTATCAAATAGACAATATAAC
                              351                                                400
SEQ ID NO:18     (351) TCAGCATGGAGCAATGTACTGCTAATGAACGGTCCTAATCAATACAGTTG
SEQ ID NO:17     (351) TCAGCATGGAGCAATGTACTGCTAATGAACGGTCCTAATCAATACAGTTG
SEQ ID NO:3      (351) TCAGCATGGAGCAATGTACTGCTAATGAACGGTCCTAATCAATACAGTTG
                              401                                                450
SEQ ID NO:18     (401) GGAAGCAGTAATG---TGGAAAACACTTCCTCAGTTCAGAAGGGAACATGT
SEQ ID NO:17     (401) GGAAGCAG--------T--------------------CAGAAGGGAACATGT
SEQ ID NO:3      (401) GGAAGCAGTAATCGATGGAAAACACTTCCTCAGTTCAGAAGGGAACATGT
                              451                                                500
SEQ ID NO:18     (449) AGATGGGAAAGTAAACAGGATATATAGACACATGCAGTTAGGTCTACCAC
SEQ ID NO:17     (425) AGATGGGAAAGTAAACAGGATATATAGACACATGCAGTTAGGTCTACCAC
SEQ ID NO:3      (451) AGATGGGAAAGTAAACAGGATATATAGACACATGCAGTTAGGTCTACCAC
                              501                                                550
SEQ ID NO:18     (499) AAGA------------------------CATGCCACAGGACTAAAA
SEQ ID NO:17     (475) AAGATATATATACAAGACAGGTTTGCCTAATCCATGCCACAGGACTAAAA
SEQ ID NO:3      (501) AAGA---------------AGA--------------CATGCCACAGGACTAAAA
                              551                                                600
SEQ ID NO:18     (521) ACAGAAGCTGGGTTTGGAACAACTTATGCAGACT----GCTATCCAGATAA
SEQ ID NO:17     (525) ACAGAAGCTGGGTTTGGAACAACTTATGCAGACGCTAGCTATCCAGATAA
SEQ ID NO:3      (526) ACAGAAGCTGGGTTTGGAACAACTTATGCAGACGCTAGCTATCCAGATAA
                              601                                                650
SEQ ID NO:18     (568) ACCTTAGAGAAACAGCTATGAGAATAAGCGTCTGAAATTTGTAGTTGCCT
SEQ ID NO:17     (575) ACCTTAGAGAAACAGCTATGAGAATAAGCGTCTGAAATTTGTAGTTGCCT
SEQ ID NO:3      (576) ACCTTAGAGAAACAGCTATGAGAATAAGCGTCTGAAATTTGTAGTTGCCT
```

FIGURE 5 (Continued):

```
                          651                                                700
SEQ ID NO:18    (618)     GTTTGGAATGGCTTATGGACGACAATGAGTGTATTTTCTGGAGTAGCCTA
SEQ ID NO:17    (625)     GTTTGGAATGGCTTATGGACGACACGTA----ATTTTCTGGAGTAGCCTA
SEQ ID NO:3     (626)     GTTTGGAATGGCTTATGGACGACAAGCT----TATTTTCTGGAGTAGCCTA
                          701                                                750
SEQ ID NO:18    (668)     CAAGTACAAGCCAAGGCACATGCTGTTCCAAACTGGCCCATATTTTGCAC
SEQ ID NO:17    (671)     CAAGTACAAGCCAAGGCACATGCTGTTCCAAACTGGCCCATATTTTGCAC
SEQ ID NO:3     (673)     CAAGTACAAGCCAAGGCACATGCTGTTCCAAACTGGCCCATATTTTGCAC
                          751                                                800
SEQ ID NO:18    (718)     AACCAAAGGAAAAGAGACAGTGACATAAGAGCATCTCCAGTGATTCAGTG
SEQ ID NO:17    (721)     AACCAAAGGAAAAGAGACAGTGACATAAGAGCATCTCCAGTGATTCAGTG
SEQ ID NO:3     (723)     AACCAAAGGAAAAGAGACAGTGACATAAGAGCATCTCCAGTGATTCAGTG
                          801                                                850
SEQ ID NO:18    (768)     AGATACCCCAAAGTCATCCAAATGTCCGTTTCGGCCGAAATGGACATGCT
SEQ ID NO:17    (771)     AGATACCCCAAAGTCATCCAAATGTCCGTTTCGGCCGAAATGGACATGCT
SEQ ID NO:3     (773)     AGATACCCCAAAGTCATCCAAATGTCCGTTTCGGCCGAAATGGACATGCT
                          851                                                900
SEQ ID NO:18    (818)     GGCCAGAAAAACATCTCCCAATGGGTCTAACACCCCAAATAGATATTTTG
SEQ ID NO:17    (821)     GGCCAGAAAAACATCTCCCAATGGGC-----GATCCCAAATAGATATTTTG
SEQ ID NO:3     (823)     GGCCAGAAAAACATCTCCCAATGGGT-----TACCCCAAATAGATATTTTG
                          901                                                950
SEQ ID NO:18    (868)     TATGTTTTGTCCGGCCCAATCCCCAAACATCTCCTAAATTTGGGGCAACT
SEQ ID NO:17    (867)     TATGTTTTGTCCGGCCCAATCCCCAAACATCTCCTAAATTTGGGGCAACT
SEQ ID NO:3     (869)     TATGTTTTGTCCGGCCCAATCCCCAAACATCTCCTAAATTTGGGGCAACT
                          951                                                1000
SEQ ID NO:18    (918)     TTGCGGTGTCCAGTGTCCGGTGTCCGGGCCCACTTCTTTTTCTCCCAAGC
SEQ ID NO:17    (917)     TTGCGGTGTCCAGTGTCCGGTGTCCGGGCCCACTTCTTTTTCTCCCAAGC
SEQ ID NO:3     (919)     TTGCGGTGTCCAGTGTCCGGTGTCCGGGCCCACTTCTTTTTCTCCCAAGC
                          1001                      1034
SEQ ID NO:18    (968)     GAGCATCTTCCTCCCGAAGCACGAAGCCCCCGTC
SEQ ID NO:17    (967)     GAGCATCTTCCTCCCGAAGCACGAAGCCCCCGTC
SEQ ID NO:3     (969)     GAGCATCTTCCTCCCGAAGCACGAAGCCCCCGTC
```

ROOT-PREFERRED PROMOTER FROM A BRACHYPODIUM DISTACHYON METALLOTHIONEIN-LIKE GENE

CROSS REFERENCE TO RELATED APPLICATION

The present application claims priority to the benefit of U.S. Provisional Patent Application Ser. No. 62/147,868 filed Apr. 15, 2015, the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 36.7 KB ACII (Text) file named "77035-US-NP-20160322-Sequence-Listing-ST25.txt" created on Mar. 22, 2016.

FIELD OF THE DISCLOSURE

The present disclosure generally relates to compositions and methods for promoting transcription of a nucleotide sequence in a plant or plant cell. Some embodiments relate to a promoter from a *Brachypodium distachyon* metallothionein-like gene (mtl) that functions in plants to promote transcription of an operably linked nucleotide sequence. Particular embodiments relate to methods including a promoter (e.g., to introduce a nucleic acid molecule into a cell) and cells, cell cultures, tissues, organisms, and parts of organisms comprising a promoter, as well as products produced therefrom.

BACKGROUND

Many plant species are capable of being transformed with transgenes to introduce agronomically desirable traits or characteristics. Plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation of the plant genome results in transgenic plants that possess desirable traits and phenotypes. However, mechanisms that allow the production of transgenic plant species to highly express multiple transgenes engineered as a trait stack are desirable.

Likewise, mechanisms that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a promoter operably linked to: a polylinker sequence; a non metallothionein-like gene; or a combination of the polylinker sequence and the a non metallothionein-like gene, wherein said promoter comprises a polynucleotide sequence that has at least 90% sequence identity with SEQ ID NO:1. In some embodiments, the promoter is 2,000 bp in length. In additional embodiments, the promoter consists of a polynucleotide sequence that has at least 90% sequence identity with SEQ ID NO:1. In other embodiments, the promoter drives expression of a polynucleotide encoding a selectable maker. In further embodiments, the promoter is operably linked to a transgene. In aspects of this embodiment, the transgene encodes a selectable marker or a gene product conferring insecticidal resistance, herbicide tolerance, nitrogen use efficiency, water use efficiency, or nutritional quality. The promoter of SEQ ID NO:1 is provided for use with a 3' untranslated polynucleotide sequence (3'-UTR), the 3' untranslated polynucleotide sequence comprising a sequence that has at least 90% sequence identity with SEQ ID NO:3, wherein the 3' untranslated sequence is operably linked to said polylinker or said transgene. In other embodiments, the promoter of SEQ ID NO:1 is provided for use with a 5' untranslated polynucleotide sequence, the 5' untranslated polynucleotide sequence comprising a sequence that has at least 90% sequence identity with SEQ ID NO:4, wherein the 5' untranslated sequence is operably linked to said polylinker or said transgene. In other embodiments, the promoter of SEQ ID NO:1 further comprises an intron sequence. In a further embodiment, the promoter of SEQ ID NO:1 drives below ground tissue specific expression.

In yet another embodiment, the subject disclosure provides for a non-*Brachypodium* plant comprising a polynucleotide sequence that has at least 90% sequence identity with SEQ ID NO:1 operably linked to a transgene. In accordance with this embodiment, the plant is selected from the group consisting of maize, wheat, rice, *sorghum*, oats, rye, bananas, sugar cane, soybean, cotton, *Arabidopsis*, tobacco, sunflower, and canola. Subsequently, the non-*Brachypodium* plant that comprises the polynucleotide sequence that has at least 90% sequence identity with SEQ ID NO:1 may be a *Zea mays* plant in some embodiments. In other embodiments, the transgene is that is operably linked to the polynucleotide sequence that has at least 90% sequence identity with SEQ ID NO:1 is inserted into the genome of a plant. In some embodiments, the polynucleotide sequence having at least 90% sequence identity with SEQ ID NO:1 is a promoter and said promoter is operably linked to a transgene. In other embodiments, the non-*Brachypodium* plant comprises a 3' untranslated sequence comprising SEQ ID NO:3 or a 3' untranslated sequence that has at least 90% sequence identity with SEQ ID NO:3, wherein the 3' untranslated sequence is operably linked to said transgene. In an additional embodiment, the polynucleotide sequence that has at least 90% sequence identity with SEQ ID NO:1 drives expression of the transgene with below ground tissue specific expression. In a further embodiment, the polynucleotide sequence that has at least 90% sequence identity with SEQ ID NO:1 is 2,000 bp in length.

In an embodiment, the subject disclosure provides for a method for producing a transgenic plant cell, the method comprising the steps of: transforming a plant cell with a gene expression cassette comprising a *Brachypodium distachyon* metallothionein-like gene (mtl) promoter operably linked to at least one polynucleotide sequence of interest; isolating the transformed plant cell comprising the gene expression cassette; and, producing a transgenic plant cell comprising the *Brachypodium distachyon* metallothionein-like gene (mtl) promoter operably linked to at least one polynucleotide sequence of interest. In other embodiments, the step of transforming a plant cell is performed with a plant transformation method. The plant transformation method can be selected from the group consisting of an *Agrobacterium*-mediated transformation method, a biolistics transformation method, a silicon carbide transformation method, a protoplast transformation method, and a liposome transformation method. In other embodiments, the polynucleotide sequence of interest is constitutively expressed throughout the transgenic plant cell. In some embodiments, the polynucleotide sequence of interest is stably integrated into the genome of the transgenic plant cell. Accordingly, the method for producing a transgenic plant cell can further comprise the steps of: regenerating the transgenic plant cell into a transgenic plant; and, obtaining the transgenic plant, wherein the transgenic plant comprises the gene expression cassette comprising the *Brachypodium distachyon* metallothionein-like gene (mtl) promoter operably linked to at least one polynucleotide sequence of interest. In an embodiment, the transgenic plant cell is a monocotyledonous transgenic plant cell or a dicotyledonous transgenic plant cell. For example, the dicotyledonous transgenic plant cell can be selected from the group consisting of an *Arabidopsis* plant cell, a tobacco plant cell, a soybean plant cell, a canola plant cell, and a cotton plant cell. Further, the monocotyledonous transgenic plant cell is selected from the group consisting of a maize plant cell, a rice plant cell, and a wheat plant cell. The *Brachypodium distachyon* metallothionein-like gene (mtl) promoter used in the method may comprise the polynucleotide of SEQ ID NO:1. In embodiments, the *Brachypodium distachyon* metallothionein-like gene (mtl) promoter may further comprise a first polynucleotide sequence of interest operably linked to the 3' end of SEQ ID NO:1.

In an embodiment, the subject disclosure provides for a method for expressing a polynucleotide sequence of interest in a plant cell, the method comprising introducing into the plant cell a polynucleotide sequence of interest operably linked to a *Brachypodium distachyon* metallothionein-like gene (mtl) promoter. In some embodiments, the polynucleotide sequence of interest operably linked to the *Brachypodium distachyon* metallothionein-like gene (mtl) promoter is introduced into the plant cell by a plant transformation method. As such, the plant transformation method can be selected from the group consisting of an *Agrobacterium*-mediated transformation method, a biolistics transformation method, a silicon carbide transformation method, a protoplast transformation method, and a liposome transformation method. In embodiments, the polynucleotide sequence of interest is constitutively expressed throughout the plant cell. In some embodiments, the polynucleotide sequence of interest is stably integrated into the genome of the plant cell. As such, the transgenic plant cell is a monocotyledonous plant cell or a dicotyledonous plant cell. As an example, the dicotyledonous plant cell is selected from the group consisting of an *Arabidopsis* plant cell, a tobacco plant cell, a soybean plant cell, a canola plant cell, and a cotton plant cell. Further, the monocotyledonous plant cell is selected from the group consisting of a maize plant cell, a rice plant cell, and a wheat plant cell.

In an embodiment, the subject disclosure provides for a transgenic plant cell comprising a *Brachypodium distachyon* metallothionein-like gene (mtl) promoter. In some embodiments, the transgenic plant cell comprises a transgenic event. In an aspect of the embodiment, the transgenic event comprises an agronomic trait. Accordingly, the agronomic trait is selected from the group consisting of an insecticidal resistance trait, herbicide tolerance trait, nitrogen use efficiency trait, water use efficiency trait, nutritional quality trait, DNA binding trait, selectable marker trait, small RNA trait, or any combination thereof. In other embodiments, the agronomic trait comprises an herbicide tolerant trait. In an aspect of the embodiment, the herbicide tolerant trait comprises an aad-1 coding sequence. In some embodiments, the transgenic plant cell produces a commodity product. The commodity product is selected protein concentrate, protein isolate, grain, meal, flour, oil, or fiber. In an embodiment, the transgenic plant cell is selected from the group consisting of a dicotyledonous plant cell or a monocotyledonous plant cell. Accordingly, the monocotyledonous plant cell is a maize plant cell. In other embodiments, the *Brachypodium distachyon* metallothionein-like gene (mtl) promoter comprises a polynucleotide with at least 90% sequence identity to the polynucleotide of SEQ ID NO:1. In yet another embodiment, the *Brachypodium distachyon* metallothionein-like gene (mtl) promoter is 2,000 bp in length. In further embodiments, the *Brachypodium distachyon* metallothionein-like gene (mtl) promoter consists of SEQ ID NO:1. In additional embodiments, the *Brachypodium distachyon* metallothionein-like gene (mtl) promoter consists of SEQ ID NO:1 is operably linked to the 3' end of SEQ ID NO:1. In other embodiments the *Brachypodium distachyon* metallothionein-like gene (mtl) promoter drives expression of an agronomic trait in below ground plant tissues.

The subject disclosure provides for an isolated polynucleotide comprising a nucleic acid sequence with at least 90% sequence identity to the polynucleotide of SEQ ID NO: 1. In some embodiments, the isolated polynucleotide drives below ground tissue specific expression. In other embodiments, the isolated polynucleotide has expression activity within a plant cell. In embodiments, the isolated polynucleotide comprises an open-reading frame polynucleotide coding for a polypeptide; and a termination sequence. Further embodiments include the isolated polynucleotide comprising a nucleic acid sequence with at least 90% sequence identity to the polynucleotide of SEQ ID NO:1, wherein the polynucleotide of SEQ ID NO:1 is 2,000 bp in length.

The foregoing and other features will become more apparent from the following detailed description of several embodiments, which proceeds with reference to the accompanying figures.

Figure 1:
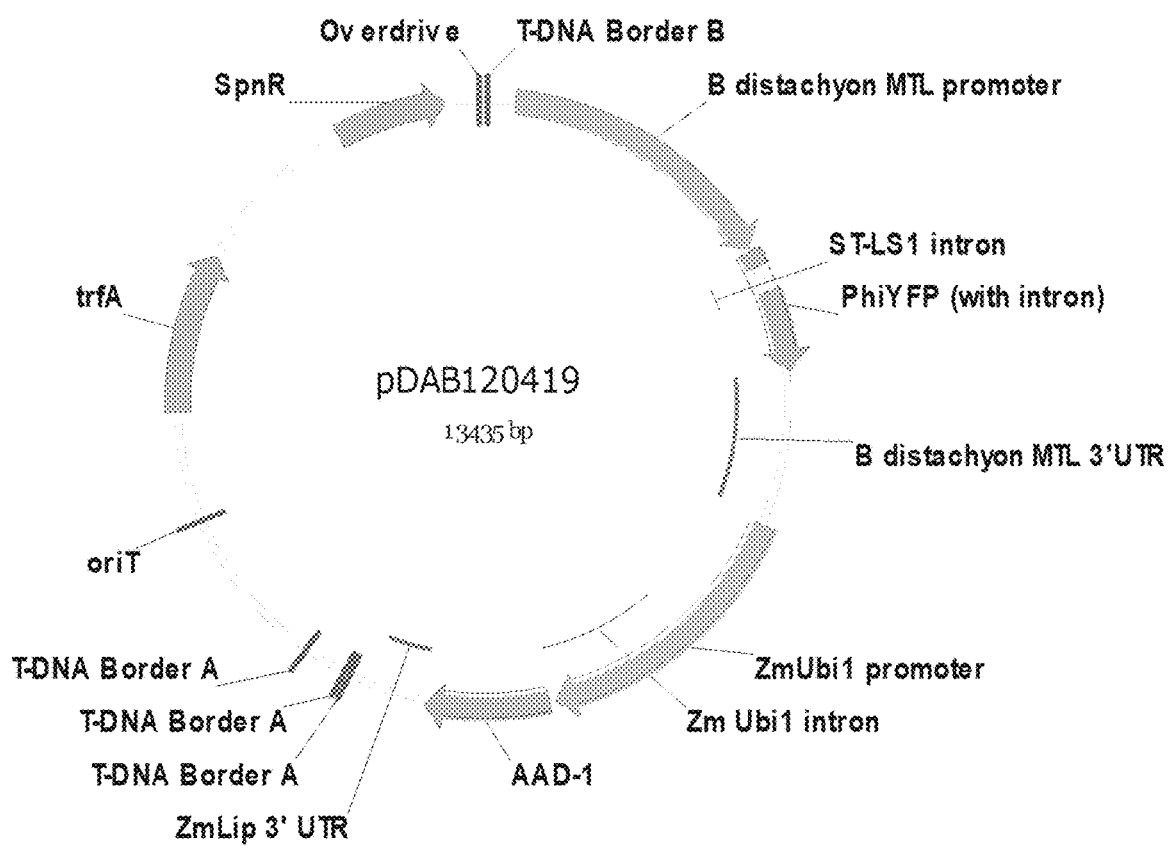
FIG. 1: This figure is a schematic of pDAB102419 which contains the *Brachypodium distachyon* metallothionein-like gene (mtl) promoter of SEQ ID NO:1 (labeled as *B distachyon* MTL Promoter) and the *Brachypodium distachyon* metallothionein-like gene (mtl) 3'-UTR of SEQ ID NO:3 (labeled as *B distachyon* MTL 3'UTR).

FIG. 2: This figure provides a polynucleotide alignment of the *Brachypodium distachyon* metallothionein-like gene (mtl) promoter of SEQ ID NO:1 (2,000 bp) and the truncated *Brachypodium distachyon* metallothionein-like gene (mtl) promoters of SEQ ID NO:7 (1,730 bp), SEQ ID NO:8 (1,530 bp), SEQ ID NO:9 (1,330 bp), SEQ ID NO:10 (1,130 bp) and SEQ ID NO:11 (1,001 bp).

FIG. 3: This figure provides a polynucleotide alignment of the *Brachypodium distachyon* metallothionein-like gene (mtl) promoter of SEQ ID NO:1 and the modified *Brachypodium distachyon* metallothionein-like gene (mtl) promoter of SEQ ID NO:12.

FIG. 4: This figure provides a polynucleotide alignment of the *Brachypodium distachyon* metallothionein-like gene (mtl) 3'-UTR of SEQ ID NO:3 and the truncated *Brachypodium distachyon* metallothionein-like gene (mtl) 3'-UTRs of SEQ ID NO:13 (264 bp), SEQ ID NO:14 (332 bp), SEQ ID NO:15 (630 bp), and SEQ ID NO:16 (727 bp).

FIG. 5: This figure provides a polynucleotide alignment of the *Brachypodium distachyon* metallothionein-like gene (mtl) 3'-UTR of SEQ ID NO:3 and the modified *Brachypodium distachyon* metallothionein-like gene (mtl) 3'-UTR of SEQ ID NO:17 and SEQ ID NO:18.

DETAILED DESCRIPTION

I. Overview of Several Embodiments

Development of transgenic plant products is becoming increasingly complex. Commercially viable transgenic plants now require the stacking of multiple transgenes into a single locus. Plant promoters used for basic research or biotechnological applications are generally unidirectional, directing only one gene that has been fused at its 3' end (downstream). Accordingly, each transgene usually requires a promoter for expression, wherein multiple promoters are required to express multiple transgenes within one gene stack. With an increasing number of transgenes in gene stacks, the same promoter is routinely used to obtain similar levels of expression patterns of different transgenes. Obtaining similar levels of transgene expression is necessary for the production of a single polygenic trait. Unfortunately, multi-gene constructs driven by the same promoter are known to cause gene silencing resulting in less efficacious transgenic products in the field. The repeated promoter elements may lead to homology-based gene silencing. In addition, repetitive sequences within a transgene may lead to gene intra locus homologous recombination resulting in polynucleotide rearrangements. The silencing and rearrangement of transgenes will likely have an undesirable affect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters are required to develop transgenic crops that drive the expression of multiple genes.

A particular problem in promoter identification is the need to identify tissue-specific promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters can be initially identified from observing the expression of genes, which are expressed in particular tissues or at particular time periods during plant development. These tissue specific promoters are required for certain applications in the transgenic plant industry and are desirable as they permit specific expression of heterologous genes in a tissue and/or developmental stage selective manner, indicating expression of the heterologous gene differentially at various organs, tissues and/or times, but not in other tissue. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters to confine the expression of the transgenes encoding an agronomic trait in specific tissues types like developing parenchyma cells. As such, a particular problem in the identification of promoters is how to identify the promoters, and to relate the identified promoter to developmental properties of the cell for specific tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." *Genome research* 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." *Molecular biotechnology* 56.1 (2014): 38-49). Existing promoter analysis tools cannot reliably identify such cis regulatory elements in a genomic sequence, thus predicting too many false positives because these tools are generally focused only on the sequence content (Fickett J W, Hatzigeorgiou A G (1997) Eukaryotic promoter recognition. Genome research 7: 861-878). Accordingly, the identification of promoter regulatory elements requires that an appropriate sequence of a specific size is obtained that will result in driving expression of an operably linked transgene in a desirable manner.

Provided are methods and compositions for overcoming such problems through the use of *Brachypodium distachyon* metallothionein-like gene (mtl) promoter regulatory elements to express transgenes in plant.

II. Terms and Abbreviations

Throughout the application, a number of terms are used. In order to provide a clear and consistent understanding of the specification and claims, including the scope to be given such terms, the following definitions are provided.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non metallothionein-like transgene" or "non metallothionein-like gene" is any transgene that has less than 80% sequence identity with the *Brachypodium distachyon* metallothionein-like gene coding sequence (SEQ ID NO:6).

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual*, 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

As used herein, the term "sequence identity" or "identity", as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) Genes & Dev., 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) Proc. Natl. Acad. Sci. USA 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3'-UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALE binding domains that can be "engineered" to bind to a predetermined nucleotide sequence. Typically, the engineered DNA binding proteins (e.g., zinc fingers, CRISPRs, or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestgris* pv. Vesicatoria (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PauI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™ etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. Constructs comprising a polylinker are utilized for the insertion and/or excision of nucleic acid sequences such as the coding region of a gene. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly®, BioBrick® Assembly, etc.). Constructs comprising a polylinker areutilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)," "tmRNA" (a.k.a. "10S RNA," Muto et al., (1998) *Trends Biochem Sci.* 23:25-29; and Gillet et al., (2001) *Mol Microbiol.* 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and Meyers (ed.), *Molecular Biology and Biotechnology: A Comprehensive Desk Reference*, VCH Publishers, Inc., 1995 (ISBN 1-56081-569-8).

As used herein, the articles, "a," "an," and "the" include plural references unless the context clearly and unambiguously dictates otherwise.

III. *Brachypodium distachyon* Metallothionein-Like Gene (Mtl) Promoter and Nucleic Acids Comprising the Same Provided are methods and compositions for using a promoter from a *Brachypodium distachyon* metallothionein-like gene (mtl) to express non metallothionein-like transgenes in plant. In an embodiment, a promoter can be the *Brachypodium distachyon* metallothionein-like gene (mtl) promoter of SEQ ID NO:1.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO: 1. In an embodiment, a promoter is a *Brachypodium distachyon* metallothionein-like gene (mtl) promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, a nucleic acid vector is provided comprising a *Brachypodium distachyon* metallothionein-like gene (mtl) promoter of SEQ ID NO: 1. In an embodiment, a polynucleotide is provided comprising a *Brachypodium distachyon* metallothionein-like gene (mtl) promoter that is operably linked to a polylinker. In an embodiment, a gene expression cassette is provided comprising a *Brachypodium distachyon* metallothionein-like gene (mtl) promoter that is operably linked to a non metallothionein-like transgene. In an embodiment, a nucleic acid vector is provided comprising a *Brachypodium distachyon* metallothionein-like gene (mtl) promoter that is operably linked to a non metallothionein-like transgene. In one embodiment, the promoter consists of SEQ ID NO: 1. In an illustrative embodiment, a nucleic acid vector comprises a *Brachypodium distachyon* metallothionein-like gene (mtl) promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

Transgene expression may also be regulated by the 3'-untranslated gene region (i.e., 3'-UTR) located downstream of the gene's coding sequence. Both a promoter and a 3'-UTR can regulate transgene expression. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene.

In an embodiment, a nucleic acid vector is provided comprising a *Brachypodium distachyon* metallothionein-like gene (mtl) promoter as described herein and a 3'-UTR. In an embodiment, the nucleic acid vector comprises a *Brachypodium distachyon* metallothionein-like gene (mtl) 3'-UTR. In an embodiment, the *Brachypodium distachyon* metallothionein-like gene (mtl) 3'-UTR is SEQ ID NO:3.

In an embodiment, a nucleic acid vector is provided comprising a *Brachypodium distachyon* metallothionein-like gene (mtl) promoter as described herein and a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to the polynucleotide of SEQ ID NO:3. In an embodiment, a nucleic acid vector is provided comprising a *Brachypodium distachyon* metallothionein-like gene (mtl) promoter as described herein and the 3'-UTR wherein the *Brachypodium distachyon* metallothionein-like gene (mtl) promoter and 3'-UTR are both operably linked to opposite ends of a polylinker. In an embodiment, a gene expression cassette is provided comprising a *Brachypodium distachyon* metallothionein-like gene (mtl) promoter as described herein and a 3'-UTR, wherein the *Brachypodium distachyon* metallothionein-like gene (mtl) promoter and 3'-UTR are both operably linked to opposite ends of a non metallothionein-like transgene. In one embodiment the 3'-UTR, consists of SEQ ID NO:3. In one embodiment, a gene expression cassette is provided comprising a *Brachypodium distachyon* metallothionein-like gene (mtl) promoter as described herein and a 3'-UTR, wherein the *Brachypodium distachyon* metallothionein-like gene (mtl) promoter comprises SEQ ID NO: 1 and the 3'-UTR comprises SEQ ID NO: 3 wherein the promoter and 3'-UTR are operably linked to opposite ends of a non metallothionein-like transgene. In an aspect of this embodiment the 3'-UTR, consists of SEQ ID NO:3. In another aspect of this embodiment the promoter consists of SEQ ID NO: 1. In an illustrative embodiment, a gene expression cassette comprises a *Brachypodium distachyon* metallothionein-like gene (mtl) 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, a selectable marker transgene, or combinations thereof. In a further embodiment the transgene is operably linked to a *Brachypodium distachyon* metallothionein-like gene (mtl) promoter and a 3'-UTR from the same metallothionein-like gene.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a *Brachypodium distachyon* metallothionein-like gene (mtl) promoter.

Transgene expression may also be regulated by a 5'-UTR region located downstream of the promoter sequence. Both a promoter and a 5'-UTR can regulate transgene expression. While a promoter is necessary to drive transcription, the presence of a 5'-UTR can increase expression levels resulting in mRNA transcript for translation and protein synthesis. A 5'-UTR gene region aids stable expression of a transgene. In a further embodiment an 5'-UTR is operably linked to a *Brachypodium distachyon* metallothionein-like gene (mtl) promoter.

A *Brachypodium distachyon* metallothionein-like gene (mtl) promoter may also comprise one or more additional sequence elements. In some embodiments, a *Brachypodium distachyon* metallothionein-like gene (mtl) promoter may comprise an exon (e.g., a leader or signal peptide such as a chloroplast transit peptide or ER retention signal). For example and without limitation, a *Brachypodium distachyon* metallothionein-like gene (mtl) promoter may encode an exon incorporated into the *Brachypodium distachyon* metallothionein-like gene (mtl) promoter as a further embodiment.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

In accordance with one embodiment a nucleic acid vector is provided comprising a recombinant gene expression cassette wherein the recombinant gene expression cassette comprises a *Brachypodium distachyon* metallothionein-like gene (mtl) promoter operably linked to a polylinker sequence, a non metallothionein-like transgene or combination thereof. In one embodiment the recombinant gene cassette comprises a *Brachypodium distachyon* metallothionein-like gene (mtl) promoter operably linked to a non metallothionein-like transgene. In one embodiment the recombinant gene cassette comprises a *Brachypodium distachyon* metallothionein-like gene (mtl) promoter as disclosed herein is operably linked to a polylinker sequence. The polylinker is operably linked to the *Brachypodium distachyon* metallothionein-like gene (mtl) promoter in a manner such that insertion of a coding sequence into one of the restriction sites of the polylinker will operably link the coding sequence allowing for expression of the coding sequence when the vector is transformed or transfected into a host cell.

In accordance with one embodiment the *Brachypodium distachyon* metallothionein-like gene (mtl) promoter comprises SEQ ID NO: 1 or a sequence that has at least 80, 85, 90, 95 or 99% sequence identity with SEQ ID NO: 1. In accordance with one embodiment the *Brachypodium distachyon* metallothionein-like gene (mtl) promoter comprises SEQ ID NO: 1 or a sequence that has 80, 85, 90, 95 or 99% sequence identity with SEQ ID NO: 1. In accordance with one embodiment the promoter sequence has a total length of no more than 1.5, 2, 2.5, 3 or 4 kb. In accordance with one embodiment the *Brachypodium distachyon* metallothionein-like gene (mtl) promoter consists of SEQ ID NO: 1 or a 2,000 bp sequence that has at least 80, 85, 90, 95 or 99% sequence identity with SEQ ID NO: 1. In accordance with one embodiment the *Brachypodium distachyon* metallothionein-like gene (mtl) promoter consists of SEQ ID NO: 1 or a 2,000 bp sequence that has 80, 85, 90, 95 or 99% sequence identity with SEQ ID NO: 1.

Further provided as an embodiment of the *Brachypodium distachyon* metallothionein-like gene (mtl) promoter is SEQ ID NO:12. This modified *Brachypodium distachyon* metallothionein-like gene (mtl) promoter sequence can be used herein to drive the expression of a transgene, and provide alternative promoter sequences that may be used instead of SEQ ID NO:1 as provided by the subject disclosure herein. The promoter polynucleotide sequences of SEQ ID NO:1 and SEQ ID NO:12 share 97.2% sequence identity. The promoter of SEQ ID NO:12 is provided as an additional embodiment of a *Brachypodium distachyon* metallothionein-like gene (mtl) promoter.

Also provided as embodiments of the *Brachypodium distachyon* metallothionein-like gene (mtl) promoter are SEQ ID NO:7 (1,730 bp), SEQ ID NO:8 (1,530 bp), SEQ ID NO:9 (1,330 bp), SEQ ID NO:10 (1,130 bp) and SEQ ID NO:11 (1,001 bp) as shown in FIG. 2. These truncated *Brachypodium distachyon* metallothionein-like gene (mtl) promoter sequences can be used herein to drive the expression of a transgene, and provide alternative promoter sequences that may be used instead of SEQ ID NO:1 as provided by the subject disclosure herein. The 1,730 bp promoter of SEQ ID NO:7 is provided as an additional embodiment of a *Brachypodium distachyon* metallothionein-like gene (mtl) promoter. In addition, the 1,530 bp promoter of SEQ ID NO:8 is provided as an additional embodiment of a *Brachypodium distachyon* metallothionein-like gene (mtl) promoter. The 1,330 bp promoter of SEQ ID NO:9 is provided as an additional embodiment of a *Brachypodium distachyon* metallothionein-like gene (mtl) promoter. Further, the 1,130 bp promoter of SEQ ID NO:10 is provided as an additional embodiment of a *Brachypodium distachyon* metallothionein-like gene (mtl) promoter. Furthermore, the 1,001 bp promoter of SEQ ID NO:9 is provided as an additional embodiment of a *Brachypodium distachyon* metallothionein-like gene (mtl) promoter.

In accordance with one embodiment a nucleic acid vector is provided comprising a gene cassette that consists of a *Brachypodium distachyon* metallothionein-like gene (mtl) promoter, a non metallothionein-like transgene and a *Brachypodium distachyon* metallothionein-like gene (mtl) 3'-UTR of SEQ ID NO: 3. In an embodiment, the *Brachypodium distachyon* metallothionein-like gene (mtl) 3'-UTR of SEQ ID NO: 3 is operably linked to the 3' end of the non metallothionein-like transgene. In a further embodiment the 3' untranslated sequence comprises SEQ ID NO: 3 or a sequence that has at least 80, 85, 90, 95, 99 or 100% sequence identity with SEQ ID NO: 3. In a further embodiment the 3' untranslated sequence comprises SEQ ID NO: 3 or a sequence that has 80, 85, 90, 95, 99 or 100% sequence identity with SEQ ID NO: 3. In accordance with one embodiment a nucleic acid vector is provided comprising a gene cassette that consists of SEQ ID NO: 1, or a 2,000 bp sequence that has at least 80, 85, 90, 95, or 99% sequence identity with SEQ ID NO: 1, a non metallothionein-like transgene and a 3'-UTR, wherein SEQ ID NO: 1 is operably linked to the 5' end of the non metallothionein-like transgene and the 3'-UTR of SEQ ID NO:3 is operably linked to the 3' end of the non metallothionein-like transgene. In accordance with one embodiment a nucleic acid vector is provided comprising a gene cassette that consists of SEQ ID NO: 1, or a 2,000 bp sequence that has 80, 85, 90, 95, or 99% sequence identity with SEQ ID NO: 1, a non metallothionein-like transgene and a 3'-UTR, wherein SEQ ID NO: 1 is operably linked to the 5' end of the non metallothionein-like transgene and the 3'-UTR of SEQ ID NO:3 is operably linked to the 3' end of the non metallothionein-like transgene. In a further embodiment the 3' untranslated sequence comprises SEQ ID NO: 3 or a sequence that has at least 80, 85, 90, 95, 99 or 100% sequence identity with SEQ ID NO: 3. In a further embodiment the 3' untranslated sequence consists of SEQ ID NO: 3, or a 1,002 bp sequence that has at least 80, 85, 90, 95, or 99% sequence identity with SEQ ID NO: 3. In a further embodiment the 3' untranslated sequence comprises SEQ ID NO: 3 or a sequence that has 80, 85, 90, 95, 99 or 100% sequence identity with SEQ ID NO: 3. In a further embodiment the 3' untranslated sequence consists of SEQ ID NO: 3, or a 1,002 bp sequence that has 80, 85, 90, 95, or 99% sequence identity with SEQ ID NO: 3.

Further provided as embodiments of the *Brachypodium distachyon* metallothionein-like gene (mtl) 3'-UTR is SEQ ID NO:17 and SEQ ID NO:18. These modified *Brachypodium distachyon* metallothionein-like gene (mtl) 3'-UTR sequences can be used herein to terminate the expression of a transgene, and provide alternative 3'-UTR sequences that may be used instead of SEQ ID NO:3 as provided by the subject disclosure herein. The 3'-UTR polynucleotide sequences of SEQ ID NO:3 and SEQ ID NO:17 share 94.2% sequence identity. The 3'-UTR polynucleotide sequences of SEQ ID NO:3 and SEQ ID NO:18 share 97.5% sequence identity. Finally, the 3'-UTR polynucleotide sequences of SEQ ID NO:18 and SEQ ID NO:17 share 92.7% sequence identity. The 3'-UTR of SEQ ID NO:17 is provided as an additional embodiment of a *Brachypodium distachyon* metallothionein-like gene (mtl) 3'-UTR. The 3'-UTR of SEQ ID NO:18 is provided as an additional embodiment of a *Brachypodium distachyon* metallothionein-like gene (mtl) 3'-UTR.

Also provided as embodiments of the *Brachypodium distachyon* metallothionein-like gene (mtl) 3'-UTR are SEQ ID NO:13 (264 bp), SEQ ID NO:14 (332 bp), SEQ ID NO:15 (630 bp), and SEQ ID NO:16 (727 bp) as shown in FIG. 4. These truncated *Brachypodium distachyon* metallothionein-like gene (mtl) 3'-UTR sequences can be used herein to terminate the expression of a transgene, and provide alternative 3'-UTR sequences that may be used instead of SEQ ID NO:3 as provided by the subject disclosure herein. The 264 bp 3'-UTR of SEQ ID NO:13 is provided as an additional embodiment of a *Brachypodium distachyon* metallothionein-like gene (mtl) 3'-UTR. In addition, the 332 bp 3'-UTR of SEQ ID NO:14 is provided as an additional embodiment of a *Brachypodium distachyon* metallothionein-like gene (mtl) 3'-UTR. The 630 bp 3'-UTR of SEQ ID NO:15 is provided as an additional embodiment of a *Brachypodium distachyon* metallothionein-like gene (mtl) 3'-UTR. Further, the 727 bp 3'-UTR of SEQ ID NO:16 is provided as an additional embodiment of a *Brachypodium distachyon* metallothionein-like gene (mtl) 3'-UTR.

In one embodiment a nucleic acid construct is provided comprising a promoter and a non metallothionein-like transgene and optionally one or more of the following elements:
 a) a 5' untranslated region;
 b) an intron; and
 c) a 3' untranslated region,
wherein,
 the promoter consists of SEQ ID NO:1 or a sequence having 98% sequence identity with SEQ ID NO:1; and
 the 3' untranslated region consists of SEQ ID NO:3 or a sequence having 98% sequence identity with SEQ ID NO:3; further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a promoter and a non metallothionein-like transgene and optionally one or more of the following elements:
 a) a 3' untranslated region,
wherein,
 the promoter consists of SEQ ID NO:1 or a sequence having 98% sequence identity with SEQ ID NO:1; and
 the 3' untranslated region consists of SEQ ID NO:3 or a sequence having 98% sequence identity with SEQ ID NO:3; further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a promoter and a polylinker and optionally one or more of the following elements:
 a) a '5 untranslated region,
 b) an intron, and
 c) a 3' untranslated region,
wherein,
 the promoter consists of SEQ ID NO:1 or a sequence having 98% sequence identity with SEQ ID NO:1; and
 the 3' untranslated region consists of SEQ ID NO:3 or a sequence having 98% sequence identity with SEQ ID NO:3; further wherein said promoter is operably linked to said polylinker and each optional element, when present, is also operably linked to both the promoter and the polylinker.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein the first T-DNA border is operably linked to one end of the gene construct, and the second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO: 1 or a sequence having 80, 85, 90, 95, or 99% sequence identity with SEQ ID NO: 1.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene encodes a selectable marker or a gene product conferring insecticidal resistance, herbicide tolerance, small RNA expression, nitrogen use efficiency, water use efficiency, or nutritional quality.

1. Insect Resistance

Various insect resistance coding sequences can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various insect resistance coding sequences can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab (truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various herbicide tolerance coding sequences can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various herbicide tolerance coding sequences can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylaminocarbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenyl-ether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Acc1-S1, Acc1-S2 and Acc1-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various agronomic trait coding sequences can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various agronomic trait coding sequences can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bio-ethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various DNA binding protein coding sequences can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various DNA binding protein coding sequences can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, Talens, CRISPRS, and meganucleases. The above list of DNA binding protein coding sequences is not meant to be limiting. Any DNA binding protein coding sequences is encompassed by the present disclosure.

5. Small RNA

Various small RNAs can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various small RNAs can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the *Brachypodium distachyon* metallothionein-like gene (mtl) promoter comprising SEQ ID NO: 1, or a sequence that has at least 80, 85, 90, 95 or 99% sequence identity with SEQ ID NO: 1. Various selectable markers also described as reporter genes can be operably linked to the *Brachypodium distachyon* metallothionein-like gene (mtl) promoter comprising SEQ ID NO: 1, or a sequence that has 80, 85, 90, 95 or 99% sequence identity with SEQ ID NO: 1. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Accl-S1, Accl-S2 and Accl-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvylshikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, or transgene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. No. 6,166,302, and U.S. Pat. No. 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. In one embodiment, a second fluorescent DNA dye is SYTO13® used at less than 10 μM, less than 4 μM, or less than 2.7 μM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoresis, followed by transfer of the electrophoretically separated components from the gels to transfer membranes that are made of materials such as nitrocellulose, polyvinylidene fluoride (PVDF), or nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transgenic Plants

In an embodiment, a plant, plant tissue, or plant cell comprises a *Brachypodium distachyon* metallothionein-like gene (mtl) promoter. In one embodiment a plant, plant tissue, or plant cell comprises the *Brachypodium distachyon* metallothionein-like gene (mtl) promoter of a sequence selected from SEQ ID NO:1 or a sequence that has at least 80%, 85%, 90%, 95% or 99.5% sequence identity with a sequence selected from SEQ ID NO:1. In one embodiment a plant, plant tissue, or plant cell comprises the *Brachypodium distachyon* metallothionein-like gene (mtl) promoter of a sequence selected from SEQ ID NO:1 or a sequence that has 80%, 85%, 90%, 95% or 99.5% sequence identity with a sequence selected from SEQ ID NO:1. In another embodiment a plant, plant tissue, or plant cell comprises the *Brachypodium distachyon* metallothionein-like gene (mtl) 3'-UTR consists of a sequence selected from SEQ ID NO:3 or a sequence that has at least 80%, 85%, 90%, 95% or 99.5% sequence identity with a sequence selected from SEQ ID NO:3. In another embodiment a plant, plant tissue, or plant cell comprises the *Brachypodium distachyon* metallothionein-like gene (mtl) 3'-UTR consists of a sequence selected from SEQ ID NO:3 or a sequence that has 80%, 85%, 90%, 95% or 99.5% sequence identity with a sequence selected from SEQ ID NO:3. In an embodiment, a plant, plant tissue, or plant cell comprises a gene expression cassette comprising a sequence selected from SEQ ID NO:1, or a sequence that has at least 80%, 85%, 90%, 95% or 99.5% sequence identity with a sequence selected from SEQ ID NO:1 that is operably linked to a non-*Brachypodium distachyon* metallothionein-like transgene. In an embodiment, a plant, plant tissue, or plant cell comprises a gene expression cassette comprising a sequence selected from SEQ ID NO:1, or a sequence that has 80%, 85%, 90%, 95% or 99.5% sequence identity with a sequence selected from SEQ ID NO:1 that is operably linked to a non-*Brachypodium distachyon* metallothionein-like transgene. In an illustrative embodiment, a plant, plant tissue, or plant cell comprises a gene expression cassette comprising a *Brachypodium distachyon* metallothionein-like promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a non-endogenous *Brachypodium distachyon* metallothionein-like gene (mtl) derived promoter sequence operably linked to a transgene, wherein the *Brachypodium distachyon* metallothionein-like gene (mtl) promoter derived promoter sequence comprises a sequence SEQ ID NO:1 or a sequence having 80%, 85%, 90%, 95% or 99.5% sequence identity with SEQ ID NO:1. In one embodiment a plant, plant tissue, or plant cell is provided wherein the plant, plant tissue, or plant cell comprises SEQ ID NO: 1, or a sequence that has at least 80%, 85%, 90%, 95% or 99.5% sequence identity with SEQ ID NO: 1 operably linked to a non-*Brachypodium distachyon* metallothionein-like transgene. In one embodiment a plant, plant tissue, or plant cell is provided wherein the plant, plant tissue, or plant cell comprises SEQ ID NO: 1, or a sequence that has 80%, 85%, 90%, 95% or 99.5% sequence identity with SEQ ID NO: 1 operably linked to a non-*Brachypodium distachyon* metallothionein-like transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, *sorghum*, oats, rye, bananas, sugar cane, soybean, cotton, sunflower, and canola. In one embodiment the plant is *Zea mays*. In accordance with one embodiment the plant, plant tissue, or plant cell comprises SEQ ID NO: 1 or a sequence having 80%, 85%, 90%, 95% or 99.5% sequence identity with SEQ ID NO:1 operably linked to a non-*Brachypodium distachyon* metallothionein-like transgene. In one embodiment the plant is *Zea mays*. In accordance with one embodiment the plant, plant tissue, or plant cell comprises SEQ ID NO: 1 or a sequence having at least 80%, 85%, 90%, 95% or 99.5% sequence identity with SEQ ID NO:1 operably linked to a non-*Brachypodium distachyon* metallothionein-like transgene. In one embodiment the plant, plant tissue, or plant cell comprises a promoter operably linked to a transgene wherein the promoter consists of SEQ ID NO: for a sequence having 80%, 85%, 90%, 95% or 99.5% sequence identity with SEQ ID NO: 1. In one embodiment the plant, plant tissue, or plant cell comprises a promoter operably linked to a transgene wherein the promoter consists of SEQ ID NO: for a sequence having at least 80%, 85%, 90%, 95% or 99.5% sequence identity with SEQ ID NO: 1. In accordance with one embodiment the gene construct comprising *Brachypodium distachyon* metallothionein-like derived promoter sequence operably linked to a transgene is incorporated into the genome of the plant, plant tissue, or plant cell.

In one embodiment a non-*Brachypodium* plant, plant tissue, or plant cell is provided comprising SEQ ID NO: 1, or a sequence that has at least 80%, 85%, 90%, 95% or 99.5% sequence identity with SEQ ID NO:1, operably linked to a transgene. In one embodiment a non-*Brachypodium* plant, plant tissue, or plant cell is provided comprising SEQ ID NO: 1, or a sequence that has 80%, 85%, 90%, 95% or 99.5% sequence identity with SEQ ID NO:1, operably linked to a transgene. In accordance with one embodiment the non-*Brachypodium* plant, plant tissue, or plant cell is a dicotyledonous or monocotyledonous plant or plant cell or tissue derived from a dicotyledonous or monocotyledonous plant. In one embodiment the plant is selected from the group consisting of maize, wheat, rice, *sorghum*, oats, rye, bananas, sugar cane, soybean, cotton, sunflower, and canola. In one embodiment the plant is *Zea mays*. In accordance with one embodiment the promoter sequence operably linked to a transgene is incorporated into the genome of the plant, plant tissue, or plant cell.

In one embodiment a non-*Brachypodium* plant, plant tissue, or plant cell is provided that comprises SEQ ID NO: 1, or a sequence that has at least 80%, 85%, 90%, 95% or 99.5% sequence identity with SEQ ID NO:1, operably linked to the 5' end of a transgene and a 3' untranslated sequence comprising SEQ ID NO: 3 or a sequence that has at least 80%, 85%, 90%, 95% or 99.5% sequence identity with SEQ ID NO:3, wherein the 3' untranslated sequence is operably linked to said transgene. In accordance with one embodiment the non-*Brachypodium* plant, plant tissue, or plant cell is a dicotyledonous or monocotyledonous plant or is a plant issue or cell derived from a dicotyledonous or monocotyledonous plant. In one embodiment the plant is selected from the group consisting of maize, wheat, rice, *sorghum*, oats, rye, bananas, sugar cane, soybean, cotton, sunflower, and canola. In one embodiment the plant is *Zea mays*. In accordance with one embodiment the promoter sequence operably linked to a transgene is incorporated into the genome of the plant, plant tissue, or plant cell.

In an embodiment, a plant, plant tissue, or plant cell according to the methods disclosed herein can be a monocotyledonous plant. The monocotyledonous plant, plant tissue, or plant cell can be, but not limited to corn, rice, wheat, sugarcane, barley, rye, *sorghum*, orchids, bamboo, banana, cattails, lilies, oat, onion, millet, switchgrass, turfgrass, and triticale.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene or gene construct containing the gene regulatory elements of the subject disclosure. The present disclosure further encompasses the progeny, clones, cell lines or cells of the transgenic plants described above wherein said progeny, clone, cell line or cell has the transgene or gene construct containing the gene regulatory elements of the subject disclosure.

The present disclosure also encompasses the cultivation of transgenic plants described above, wherein the transgenic plant has the transgene or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene in a plant comprises growing a plant comprising a *Brachypodium distachyon* metallothionein-like gene (mtl) promoter operably linked to at least one transgene or a polylinker sequence. In an embodiment, a method of expressing at least one transgene in a plant comprising growing a plant comprising a *Brachypodium distachyon* metallothionein-like gene (mtl) promoter 3'-UTR operably linked to at least one transgene or a polylinker sequence. In one embodiment the *Brachypodium distachyon* metallothionein-like gene (mtl) promoter consists of a sequence selected from SEQ ID NO:1 or a sequence that has at least 80%, 85%, 90%, 95% or 99.5% sequence identity with a sequence selected from SEQ ID NO:1. In another embodiment the *Brachypodium distachyon* metallothionein-like gene (mtl) 3'-UTR consists of a sequence selected from SEQ ID NO:3 or a sequence that has at least 80%, 85%, 90%, 95% or 99.5% sequence identity with a sequence selected from SEQ ID NO:3. In an embodiment, a method of expressing at least one transgene in a plant comprising growing a plant comprising a *Brachypodium distachyon* metallothionein-like gene (mtl) promoter and a *Brachypodium distachyon* metallothionein-like gene (mtl) 3'-UTR operably linked to at least one transgene. In an embodiment, a method of expressing at least one transgene in a plant tissue or plant cell comprising culturing a plant tissue or plant cell comprising a *Brachypodium distachyon* metallothionein-like gene (mtl) promoter operably linked to at least one transgene. In an embodiment, a method of expressing at least one transgene in a plant tissue or plant cell comprising culturing a plant tissue or plant cell comprising a *Brachypodium distachyon* metallothionein-like gene (mtl) promoter 3'-UTR operably linked to at least one transgene. In an embodiment, a method of expressing at least one transgene in a plant tissue or plant cell comprising culturing a plant tissue or plant cell comprising a *Brachypodium distachyon* metallothionein-like gene (mtl) promoter and a *Brachypodium distachyon* metallothionein-like gene (mtl) 3'-UTR operably linked to at least one transgene.

In an embodiment, a method of expressing at least one transgene in a plant comprises growing a plant comprising a gene expression cassette comprising a *Brachypodium distachyon* metallothionein-like gene (mtl) promoter operably linked to at least one transgene. In one embodiment the *Brachypodium distachyon* metallothionein-like gene (mtl) promoter consists of a sequence selected from SEQ ID NO:1 or a sequence that has at least 80%, 85%, 90%, 95% or 99.5% sequence identity with a sequence selected from SEQ ID NO:1. In one embodiment the *Brachypodium distachyon* metallothionein-like gene (mtl) promoter consists of a sequence selected from SEQ ID NO:1 or a sequence that has 80%, 85%, 90%, 95% or 99.5% sequence identity with a sequence selected from SEQ ID NO:1. In another embodiment the *Brachypodium distachyon* metallothionein-like gene (mtl) 3'-UTR consists of a sequence selected from SEQ ID NO:3 or a sequence that has at least 80%, 85%, 90%, 95% or 99.5% sequence identity with a sequence selected from SEQ ID NO:3. In another embodiment the *Brachypodium distachyon* metallothionein-like gene (mtl) 3'-UTR consists of a sequence selected from SEQ ID NO:3 or a sequence that has 80%, 85%, 90%, 95% or 99.5% sequence identity with a sequence selected from SEQ ID NO:3. In an embodiment, a method of expressing at least one transgene in a plant comprises growing a plant comprising a gene expression cassette comprising a *Brachypodium distachyon* metallothionein-like gene (mtl) promoter and a *Brachypodium distachyon* metallothionein-like gene (mtl) 3'-UTR operably linked to at least one transgene. In an embodiment, a method of expressing at least one transgene in a plant comprises growing a plant comprising a gene expression cassette comprising a *Brachypodium distachyon* metallothionein-like gene (mtl) 3'-UTR operably linked to at least one transgene. In an embodiment, a method of expressing at least one transgene in a plant tissue or plant cell comprises culturing a plant tissue or plant cell comprising a gene expression cassette containing a *Brachypodium distachyon* metallothionein-like gene (mtl) promoter operably linked to at least one transgene. In an embodiment, a method of expressing at least one transgene in a plant tissue or plant cell comprises culturing a plant tissue or plant cell comprising a gene expression cassette containing a *Brachypodium distachyon* metallothionein-like gene (mtl) 3'-UTR operably linked to at least one transgene. In an embodiment, a method of expressing at least one transgene in a plant tissue or plant cell comprises culturing a plant tissue or plant cell comprising a gene expression cassette, a *Brachypodium distachyon* metallothionein-like gene (mtl) promoter and a *Brachypodium distachyon* metallothionein-like gene (mtl) 3'-UTR operably linked to at least one transgene.

The following examples are provided to illustrate certain particular features and/or embodiments. The examples should not be construed to limit the disclosure to the particular features or embodiments exemplified.

EXAMPLES

Example 1: A Promoter from a *Brachypodium distachyon* Metallothionein-Like Gene (Mtl)

The promoter from a *Brachypodium distachyon* metallothionein-like gene (mtl) (SEQ ID NO:1) is a 2,000 bp polynucleotide sequence that was identified from the *Brachypodium distachyon* genomic DNA (gDNA) sequence. The promoter sequence was identified by BLASTing the Phytozome database (Goodstein et al., 2012) with a *Zea mays* metallothionein-like gene (mtl). The resulting hits were analyzed and a single coding sequence was selected for further analysis. From the assessment of the contiguous chromosomal sequence that spanned millions of base pairs, a 2,000 bp polynucleotide sequence was identified and isolated for use in expression of heterologous coding sequences. This novel polynucleotide sequence was analyzed for use as a regulatory sequence to drive expression of a gene. As shown in the sequence (SEQ ID NO:2) below, the 2,000 bp *Brachypodium distachyon* metallothionein-like gene (mtl) promoter of SEQ ID NO:1 is provided as base pairs 1-2,000. The native mtl gene coding sequence of SEQ ID NO:6 is provided as base pairs 2,001-2,345. The 1,002 bp *Brachypodium distachyon* metallothionein-like gene (mtl) 3'-UTR of SEQ ID NO:3 is provided as base pairs 2,346-3,347. Accordingly, SEQ ID NO:2 is provided as:

```
tttcgtgtgcttacttggggcttcctttgggcctgcggaagcagacggcg
tgccagctgagaccgttggtggacaatgtggatggacgtctagcttcgtg
gaaggcccttctcctttccaagggaggatgactggtgctggtcaagtcca
ccctgacagcgatgccggtctactcgatgatgtcactcgacctttcggac
aagatcatcaaaggggtggacaagatctgtcgtggtttcctttggcgtgg
tcagaaggacgctaaaggggggggggcattgtatggtggcttgggtcgtg
gtgtgttcgccgaagccttcggtggactcggaattccaaatcttcgcat
gctcaacgaggccttgagggtccgctagaggtggcttgagagggtggacg
attccaaaccatgggtcggtttcaaggttgagacgcccagaggtctatgt
tatctttgaggcggccacttcctctttggtgggcgatggccggaagaccc
tcttctggaccgatcgttggctgcatggcgtctgttttcgagatgcgttc
ctgatcctcgtgggccatgtttgccacaagttttgcgcacgcgcacagt
gcgggaggctctgcatggagcgtggactggcgacatgggtccagacctaa
agggaagctactcttgaggagttcctcactctctgggactggcttcgtgg
ggtccaactggaagaagggagggccgactctcttcattggaactggtctc
gtggtgatagttactcggcaaagactgcttatgcgaatctcttcactggc
cgcatggttgacccgttagcggctgagatctagggcttcggagaggtgtc
gtttcttcgtctggctcgcagttcgaaatagatgctagacggcggatcgc
```

-continued

```
ttgcgaggcgtgggcttccccaccctgacaagtgtcaggagatggagacc atttcccatctactcttggggtgtgtcttggcgaggcaggtttgggagcg cttgtgggcggcttggggacacgtggagtgggctccgaatgcggatgcta ctctgcgggaatggtggtcttctcttcccttaccacggcgagcccggagg gacttccggacgggatcatacttgttcttggaccatttggtgccattg gaatgatgtggccttccttgcagcttgtcgtgcttcgcctccaggaggag tttggtcggtgggcgcacgccggcctcttaggggtagagtgtctattcc agccttgatggtgagtggttggatagctagcacatagtcttttttctct ttcttgccacttggtgatgttgtattgccgcttcggcgttgtactagcct tctggctcttcttatttaatcgatgatgcacccgctgggtggcattcttg aaattttttgagaaaatactcctacaaaggaagtacagtaatttgatac acaatgcttctctaaatacgaaaatacaaacatcctaatgttattccaa ctatgctactccctccgttcctaaactcttatctttgttttgttcaaat ttgtaccaaacaacgacaaaaatttagtaacggaggaagtatatatacga agtgataccaaataaggtgtttctttacttgaaagctagttcctctgagg taaaagaaatgatgaggatcaaggaaggcccatttcttgccggcacgcag ttgccgaagtcagtagatttaaaatgacctcacatactgaagaaggaaag ggaagttaaccacgccattgttgctttagcagaaagcaaccatatcctaa ttaacatcacagtacacgttgaaacggcagggcacgataattggtgaaga ctgattccagggagcatcgtggcacgcaaaaacgcccttgccttgttccc ttataaatagtggtgcagaagatacatttgtgatcaccatctcaaagcgc ctctttattcccctttcatcttgagcttaagtactagagaaaaattaagg atgtcttgcagctgtggatctggatgcagctgcggctcaaactgcacctg cgggtatgtatagatgcttaattctgtgttgcagattactacgtagctgc taataccatctaagtaatgacaatgctttctcatgatgatcaattttcat ttgctgtgtggttcagcaagatgtaccctgacttggcagagaagagcggc ggcacccagcaggccaccaccatgatcctcggcgttgcgcctgctaaggc ccagtttgaggaggccgccgagtccggtgaggccggccatggctgcagct gcggcgccaactgcaagtgcgaccgtgcaactgctaagatgcacgcgac gcgctgctgcttgtggtgtgtgtttgtgtgatctcgactgaataaaaggg acacggtacatccggggttggttggtgctcgagtcgagtgtgcaaggttg tgtggtttgccagctcttggtgtgtgtctccttgtgctcatgtgacttgt gaaaccattaatagtaaccactttgtgcttgtgtgtgtgtgggcacctgt gtttctgtaatggtctatctggagtgaatatatacaagacaggtttgcct aaccatgccttttccttccttgaggtcatcgcgccaacacgaatgacgag aaccaatgatcttaggactatcaaatagacaatataactcagcatggagc aatgtactgctaatgaacggtcctaatcaatacagttgggaagcagtaat cgatggaaaacacttcctcagttcagaagggaacatgtagatgggaaagt aaacaggatatatagacacatgcagttaggtctaccacaagaagacatgc cacaggactaaaaacagaagctgggtttggaacaacttatgcagacgcta gctatccagataaaccttagagaaacagctatgagaataagcgtctgaaa tttgtagttgcctgtttggaatggcttatggacgacaagcttattttctg gagtagcctacaagtacaagccaaggcacatgctgttccaaactggccca tattttgcacaaccaaaggaaaagagacagtgacataagagcatctccag tgattcagtgagataccccaaagtcatccaaatgtccgtttcggccgaaa tggacatgctggccagaaaaacatctcccaatgggttaccccaaatagat attttgtatgttttgtccggcccaatccccaaacatctcctaaatttggg gcaactttgcggtgtccagtgtccggtgtccgggcccacttctttttctc ccaagcgagcatcttcctcccgaagcacgaagcccccgtc
```

Example 2: Vector Construction

The following vectors were built to incorporate the promoter from a *Brachypodium distachyon* metallothionein-like gene (mtl) upstream of a transgene. The vector construct pDAB120419 contained a gene expression cassette, in which the phi-yfp transgene (Phi-yellow fluorescent protein; Clontech, Mountain View, Calif.) was driven by the promoter from a *Brachypodium distachyon* metallothionein-like gene (mtl) of SEQ ID NO:1 and flanked by the *Brachypodium distachyon* metallothionein-like gene (mtl) 3'-UTR of SEQ ID NO:3. A diagram of this gene expression cassette is shown in FIG. 1 and is provided as SEQ ID NO:4. The vector also contained a selectable marker gene expression cassette that contained the aad-1 transgene (U.S. Pat. No. 7,838,733) driven by the *Zea mays* Ubiquitin 1 promoter (Christensen et al., (1992) *Plant Molecular Biology* 18; 675-689) and was terminated by the *Zea mays* Lipase 3'-UTR (U.S. Pat. No. 7,179,902). A diagram of this gene expression cassette is shown in FIG. 1 and is provided as SEQ ID NO:5. This construct was built by synthesizing the newly designed promoter from a *Brachypodium distachyon* metallothionein-like gene by an external provider (Geneart via Life Technologies, Carlsbad, Calif.), and cloning the promoter into a Gateway™ (Life Technologies) donor vector using the GeneArt® Seamless Cloning and Assembly Kit (Life technologies) and restriction enzymes. The resulting donor vector was integrated into a final binary destination vector using the Gateway™ cloning system (Life Technologies). Clones of pDAB120419 were obtained and confirmed via restriction enzyme digestions and sequencing. The resulting construct contained a promoter that could robustly drive expression of a transgenes which was operably linked to the 3' end of the promoter.

Example 3: Modified *Brachypodium distachyon* Metallothionein-Like Gene (Mtl) Regulatory Elements The 2,000 bp *Brachypodium distachyon* metallothionein-like gene (mtl) promoter of SEQ ID NO:1 was modified by making alterations to the promoter sequence. A variant was designed and provided as SEQ ID NO:12. An alignment comparing the modified *Brachypodium distachyon* metallothionein-like gene (mtl) promoter of SEQ ID NO:1 and the modified *Brachypodium distachyon* metallothionein-like gene (mtl) promoter of SEQ ID NO:12 is provided in FIG. 3. As shown in FIG. 3 the promoter polynucleotide sequences of SEQ ID NO:1 and SEQ ID NO:12 share 97.2% sequence identity. Herein are provide novel promoter sequences that originated from the *Brachypodium distachyon* metallothionein-like gene (mtl) promoters of SEQ ID NO:1. In an embodiment, the novel promoter polynucleotide sequence of SEQ ID NO:12 can be used in a gene expression cassette to drive the expression of transgenes. In another aspect of this embodiment, the novel promoter polynucleotide sequence of SEQ ID NO:12 can be operably linked to a gene of interest and flanked by a 3'-UTR, for example the 3'-UTR of SEQ ID NO:3, and can be used in a gene expression cassette to drive the expression of transgenes.

The 1,002 bp *Brachypodium distachyon* metallothionein-like gene (mtl) 3'-UTR of SEQ ID NO:3 was modified by making alterations to the 3'-UTR sequence. New variants were designed and are provided as SEQ ID NO:17 and SEQ ID NO:18. An alignment comparing the modified *Brachypodium distachyon* metallothionein-like gene (mtl) 3'-UTR of SEQ ID NO:3 and the modified *Brachypodium distachyon* metallothionein-like gene (mtl) 3'-UTRs of SEQ ID NO:17 and SEQ ID NO:18 is provided in FIG. 5. As shown in FIG. 5 the 3'-UTR polynucleotide sequences of SEQ ID NO:3 and SEQ ID NO:17 share 94.2% sequence identity. Depicted in FIG. 5 are the 3'-UTR polynucleotide sequences of SEQ ID NO:3 and SEQ ID NO:18 which share 97.5% sequence identity. Finally, FIG. 5 presents the 3'-UTR polynucleotide sequences of SEQ ID NO:18 and SEQ ID NO:17 which share 92.7% sequence identity. Herein is provided a novel 3'-UTR sequence that originated from the *Brachypodium distachyon* metallothionein-like gene (mtl) 3'-UTR of SEQ ID NO:3. In an embodiment, the novel 3'-UTR polynucleotide sequence of SEQ ID NO:17 can be used in a gene expression cassette to terminate the expression of transgenes. In another aspect of this embodiment, the novel 3'-UTR polynucleotide sequence of SEQ ID NO:17 can be operably linked to a transgene driven by a promoter, for example the promoter of SEQ ID NO:1, and can be used in a gene expression cassette to drive the expression of transgenes. In a further embodiment, the novel 3'-UTR polynucleotide sequence of SEQ ID NO:18 can be used in a gene expression cassette to terminate the expression of transgenes. In another aspect of this embodiment, the novel 3'-UTR polynucleotide sequence of SEQ ID NO:18 can be operably linked to a transgene driven by a promoter, for example the promoter of SEQ ID NO:1, and can be used in a gene expression cassette to drive the expression of transgenes.

Example 4: Maize Transformation

Transformation of *Agrobacterium tumefaciens*:

The binary expression vector was transformed into *Agrobacterium tumefaciens* strain DAt13192 (RecA deficient ternary strain) (Int'l. Pat. Pub. No. WO2012016222). Bacterial colonies were selected, and binary plasmid DNA was isolated and confirmed via restriction enzyme digestion.

*Agrobacterium* Culture Initiation:

*Agrobacterium* cultures were streaked from glycerol stocks onto AB minimal medium (Gelvin, S., 2006, *Agrobacterium* Virulence Gene Induction, in Wang, K., ed., *Agrobacterium Protocols Second Edition Vol.* 1, Humana Press, p. 79; made without sucrose and with 5 g/L glucose and 15 g/L Bacto™ Agar) and incubated at 20° C. in the dark for 3 days. *Agrobacterium* cultures were then streaked onto a plate of YEP medium (Gelvin, S., 2006, *Agrobacterium* Virulence Gene Induction, in Wang, K., ed., *Agrobacterium Protocols Second Edition Vol.* 1, Humana Press, p. 79) and incubated at 20° C. in the dark for 1 day.

On the day of an experiment, a mixture of Inoculation medium (2.2 g/L MS salts, 68.4 g/L sucrose, 36 g/L glucose, 115 mg/L L-proline, 2 mg/L glycine, 100 mg/L myo-Inositol, 0.05 mg/L nicotinic acid, 0.5 mg/L pyridoxine HCl, 0.5 mg/L thiamine HCl) and acetosyringone was prepared in a volume appropriate to the size of the experiment. A 1 M stock solution of acetosyringone in 100% dimethyl sulfoxide was added to the Inoculation medium to make a final acetosyringone concentration of 200 μM.

For each construct, 1-2 loops of *Agrobacterium* from the YEP plate were suspended in 15 ml of the inoculation medium/acetosyringone mixture inside a sterile, disposable, 50 ml centrifuge tube and the optical density of the solution at 600 nm (O.D.$_{600}$) was measured in a spectrophotometer. The suspension was then diluted down to 0.25-0.35 O.D.$_{600}$ using additional Inoculation medium/acetosyringone mixture. The tube of *Agrobacterium* suspension was then placed horizontally on a platform shaker set at about 75 rpm at room temperature for between 1 and 4 hours before use.

Maize Transformation:

Experimental constructs were transformed into maize via *Agrobacterium*-mediated transformation of immature embryos isolated from the inbred line, *Zea mays* c.v. B 104. The method used is similar to those published by Ishida et al., (1996) Nature Biotechnol 14:745-750 and Frame et al., (2006) Plant Cell Rep 25: 1024-1034, but with several modifications and improvements to make the method amenable to high-throughput transformation. An example of a method used to produce a number of transgenic events in maize is given in U.S. Pat. App. Pub. No. US 2013/0157369 A1, beginning with the embryo infection and co-cultivation steps.

Putative T$_0$ transgenic plantlets were transplanted from Phytatrays™ (Sigma-Aldrich; St. Louis, Mo.) to small 3.5" plastic pots (T. O. Plastics; Clearwater, Minn.) filled with growing media (Premix BX; Premier Tech Horticulture), covered with humidomes (Arco Plastics Ltd.), and then hardened-off in a growth room (28° C. day/24° C. night, 16-hour photoperiod, 50-70% RH, 200 μEm-2 sec-1 light intensity). When plants reached the V3-V4 developmental stage (3-4 leaf collars visible), they were transplanted into Sunshine Custom Blend 160 soil mixture and grown to flowering in the greenhouse (Light Exposure Type: Photo or Assimilation; High Light Limit: 1200 PAR; 16-hour day length; 27° C. day/24° C. night). The plants were analyzed for transgene copy number by qPCR assays using primers designed to detect relative copy numbers of the transgenes, and putative single copy events selected for advancement were transplanted into 5 gallon pots.

Example 5: Molecular Confirmation of Copy Number

The stable integration of the phi-yfp transgene within the genome of the transgenic *Z. mays* plants was confirmed via a hydrolysis probe assay. Stably-transformed transgenic *Z. mays* plantlets that developed from the callus were obtained and analyzed to identify events that contained a low copy number (1-2 copies) of full-length T-strand inserts. Identified plantlets were advanced to the green house and grown.

The Roche Light Cycler480™ system was used to determine the transgene copy number. The method utilized a biplex TaqMan® reaction that employed oligonucleotides specific to the phi-yfp gene and to the endogenous *Z. mays* reference gene, invertase (Genbank Accession No: U16123.1), in a single assay. Copy number and zygosity were determined by measuring the intensity of phi-yfp specific fluorescence, relative to the invertase-specific fluorescence, as compared to known copy number standards.

A phi-yfp gene-specific DNA fragment was amplified with one TaqMan® primer/probe set containing a probe labeled with FAM™ fluorescent dye, and invertase was amplified with a second TaqMan® primer/probe set containing a probe labeled with HEX™ fluorescence. Copy number and zygosity of the samples were determined by measuring the relative intensity of fluorescence specific for the reporter gene, phi-yfp, to fluorescence specific for the reference gene, invertase, as compared to known copy number standards.

Example 6: Molecular Confirmation of Protein Expression

Protein Extraction:

Nunc® 96-well Maxi-Sorp Plates (Thermo Fisher Scientific Inc., Rockford, Ill.) were used for ELISA. The plates were coated with mouse monoclonal anti Phi-YFP capture antibody (OriGene Technologies Inc., Rockville, Md.). The antibody was diluted in PBS (1 µg/mL) and 150 µL of diluted PBS was added per well. The plates were incubated overnight at 4° C. The plates were kept at room temperature for 20-30 minutes before washing 4× with 350 µL of wash buffer [1×PBS supplemented with 0.05% Tween®-20 (Sigma-Aldrich, St. Louis, Mo.)]. Next, the plates were blocked with 200 µL per well of blocking buffer [1×PBS supplemented with 0.05% Tween®-20 plus 0.5% BSA (Millipore Probumin®)] for a minimum of 1 hr at +37° C. followed by 4× washing with 350 µL of wash buffer (Tomtec QuadraWash™ 2, Tomtec, Inc., Hamden, Conn.).

For the Phi-YFP ELISA, Evrogen recombinant Phi-YFP 1 mg/mL (Axxora LLC, Farmingdale, N.Y.) was used as a standard. A 5-parameter fit standard curve (between the 1 ng/ml and 0.125 ng/ml standards) was used to ensure all data fall in the linear portion of the curve. Next, 100 µL of standard or sample was added to the well. A minimum 1:4 dilution of sample in the Assay Buffer was used. Plates were incubated for 1 hour at RT on plate shaker (250 rpm; Titer Plate shaker) followed by 4× washing with 350 µL of wash buffer (Tomtec QuadraWash™ 2). About 100 µL of 1 µg/mL Evrogen rabbit polyclonal anti Phi-YFP primary antibody (Axxora) was added to each well. Plates were incubated for 1 hour at room temperature on a plate shaker at 250 rpm followed by 4× washing with 350 µL of wash buffer (Tomtec QuadraWash™ 2). Next, 100 µL of anti-rabbit IgG HRP secondary antibody (Thermo Scientific) diluted 1:5000 in Blocking/Assay buffer, which was added to each well. Plates were incubated for 1 hour at room temperature on plate shaker at 250 rpm followed by 4× washes with 350 µL of wash buffer (Tomtec QuadraWash™ 2). Then 100 µL of Pierce 1 Step Ultra TMB ELISA™ (Thermo Scientific) substrate was added in the well with gentle shaking for 10 minutes. The reaction was stopped by adding 50 µL of 0.4N $H_2SO_4$. Absorbance was read at 450 nm with a 650 nm reference filter.

The Phi-YFP expression levels were determined by ELISAs using kits from Acadia BioSciences (Portland, Me.). The ELISAs were performed using multiple dilutions of the extracts and using the reagents and instructions provided by the supplier. The protein levels were normalized using total soluble protein assay, performed using the 660 nm protein assay reagent supplied by Thermo Scientific and following the supplier's instructions.

Example 7: Expression of Genes Operably Linked to the Promoter from a *Brachypodium distachyon* Metallothionein-Like Gene (Mtl)

Maize plants were transformed with a gene expression construct that contained the promoter from a *Brachypodium distachyon* metallothionein-like gene (mtl) as described above. The ELISA analysis confirmed that the novel promoter drove robust expression of a transgene. The quantitative measurements of Phi-YFP protein obtained from transgenic plants comprising novel promoter constructs are shown in TABLE 1. The data show that Phi-YFP protein in the plants containing the novel *Brachypodium distachyon* metallothionein-like gene (mtl) promoter (i.e., pDAB120419) is expressed preferentially higher in root tissue as compared to the leaf tissue.

TABLE 1

*B. distachyon* MTL Promoter T0 Expression of Phi-YFP and AAD1

| | | PhiYFP (ng/mg) | | AAD1 (ng/mg) | |
|---|---|---|---|---|---|
| Construct | Event | Leaf | Root | Leaf | Root |
| 120419 | 120419[1]-002.001 | 3 | ND | 107 | ND |
| 120419 | 120419[1]-003.001 | 3 | ND | 116 | ND |
| 120419 | 120419[1]-005.001 | 3 | ND | 392 | ND |
| 120419 | 120419[1]-007.001 | 3 | 22 | 149 | 129 |
| 120419 | 120419[1]-010.001 | 3 | ND | 110 | ND |
| 120419 | 120419[1]-011.001 | 3 | 55 | 111 | 62 |
| 120419 | 120419[1]-014.001 | 3 | ND | 162 | ND |
| 120419 | 120419[1]-017.001 | 3 | ND | 324 | ND |
| 120419 | 120419[1]-018.001 | 3 | 607 | 412 | 372 |
| 120419 | 120419[1]-023.001 | 3 | ND | 103 | ND |
| 120419 | 120419[1]-024.001 | 3 | ND | 107 | ND |
| 120419 | 120419[1]-026.001 | 3 | 346 | 289 | 147 |
| 120419 | 120419[1]-027.001 | 3 | 234 | 415 | 177 |
| 120419 | 120419[1]-031.001 | 3 | 41 | 900 | 233 |
| 120419 | 120419[1]-032.001 | 3 | ND | 175 | ND |
| 120419 | 120419[1]-033.001 | 3 | ND | 313 | ND |
| 120419 | 120419[1]-035.001 | 3 | 79 | 651 | 210 |

ND—Not Determined

To single transgene copy plants containing a stably integrated pDAB120419 transgenic event were backcrossed to wild type B 104 corn plants to obtain $T_1$ seed that were grown to mature plants. From these mature plants, hemizygous $T_1$ plants were used for analysis to determine the expression of the AAD1 and Phi-YFP protein. Five events per construct and ten plants per event were used the protein expression analysis. Three events per construct and three to five plants per event were used for other tissue type expression. Zygosity analysis was done for Phi-YFP and AAD1. The quantitative ELISA measurements of Phi-YFP and AAD1 protein obtained from different tissue types including leaf, cob, husk, pollen, root, silk and stem tissue of $T_1$ transgenic plants comprising novel promoter constructs are shown in TABLE 2. The data confirmed the $T_0$ leaf expression results and further showed that consistent high expression of Phi-YFP protein was obtained in the primarily in root tissue types of the plants containing the novel promoter (pDAB120419). These data demonstrate that the novel promoter illustrated here drives root preferential expression of transgene in plants, and that this expression profile is heritable from a first generation to a second generation. Accordingly, the promoter from a *Brachypodium distachyon* metallothionein-like gene (mtl) is useful for biotechnological applications.

TABLE 2

Protein expression in different tissue types of transgenic corn plants

| Construct | Events | Tissue | Mean (Phi-YFP ng/mg) | Mean (AAD1 ng/mg) |
|---|---|---|---|---|
| 120419 | 120419[1]-002 | Leaf V4 | 0.3 | 34.5 |
| 120419 | 120419[1]-002 | Root V4 | 608.7 | 2419.7 |
| 120419 | 120419[1]-014 | Leaf V4 | 0.0 | 32.4 |
| 120419 | 120419[1]-014 | Root V4 | 418.0 | 2375.7 |
| 120419 | 120419[1]-023 | Cob R3 | 0.0 | 2794.7 |
| 120419 | 120419[1]-023 | Husk R3 | 0.0 | 4495.0 |
| 120419 | 120419[1]-023 | Leaf R3 | 47.4 | 1387.0 |
| 120419 | 120419[1]-023 | Leaf V12 | 0.0 | 188.3 |
| 120419 | 120419[1]-023 | Leaf V4 | 0.1 | 30.3 |
| 120419 | 120419[1]-023 | Pollen R3 | 0.0 | 1003.7 |
| 120419 | 120419[1]-023 | Root R3 | 0.0 | 355.0 |
| 120419 | 120419[1]-023 | Root V4 | 274.3 | 1536.0 |
| 120419 | 120419[1]-023 | Silk R3 | 0.7 | 4515.0 |
| 120419 | 120419[1]-023 | Stem R3 | 1.7 | 6545.7 |
| 120419 | 120419[1]-024 | Cob R3 | 0.0 | 3615.7 |
| 120419 | 120419[1]-024 | Husk R3 | 0.0 | 4998.3 |
| 120419 | 120419[1]-024 | Kernel R3 | 0.0 | 2100.0 |
| 120419 | 120419[1]-024 | Leaf R3 | 3.2 | 1498.2 |
| 120419 | 120419[1]-024 | Leaf V12 | 0.0 | 240.3 |
| 120419 | 120419[1]-024 | Leaf V4 | 0.9 | 38.8 |
| 120419 | 120419[1]-024 | Pollen R3 | 0.0 | 4313.0 |
| 120419 | 120419[1]-024 | Root R3 | 0.0 | 964.7 |
| 120419 | 120419[1]-024 | Root V4 | 132.0 | 1001.0 |
| 120419 | 120419[1]-024 | Silk R3 | 0.3 | 7784.3 |
| 120419 | 120419[1]-024 | Stem R3 | 0.0 | 5991.0 |
| 120419 | 120419[1]-033 | Cob R3 | 0.0 | 4212.7 |
| 120419 | 120419[1]-033 | Husk R3 | 0.0 | 5691.0 |
| 120419 | 120419[1]-033 | Kernel R3 | 0.0 | 1804.0 |
| 120419 | 120419[1]-033 | Leaf R3 | 0.3 | 1463.5 |
| 120419 | 120419[1]-033 | Leaf V12 | 0.0 | 398.4 |
| 120419 | 120419[1]-033 | Leaf V4 | 0.6 | 30.7 |
| 120419 | 120419[1]-033 | Pollen R3 | 0.0 | 3759.3 |
| 120419 | 120419[1]-033 | Root R3 | 0.0 | 1461.0 |
| 120419 | 120419[1]-033 | Root V4 | 787.3 | 3445.0 |
| 120419 | 120419[1]-033 | Silk R3 | 0.0 | 7656.3 |
| 120419 | 120419[1]-033 | Stem R3 | 0.0 | 6670.0 |

The Phi-YFP ELISA results indicated that the *Brachypodium distachyon* metallothionein-like gene (mtl) promoter regulatory element (SEQ ID NO:1) drove below-ground preferred expression, specifically in root tissues, of Phi-YFP in $T_0$ events that were transformed with construct, pDAB120419. Negligible expression of Phi-YFP by the *Brachypodium distachyon* metallothionein-like gene (mtl) promoter regulatory element was observed in the leaf tissues of these events (TABLE 1 and TABLE 2). The events produced from the transformation also expressed AAD1 protein in both leaf and root tissues. The expression of AAD1 within these events served as a control to compare expression levels of Phi-YFP in differing tissues. In summary, the *Brachypodium distachyon* metallothionein-like gene (mtl) promoter was developed for robust expression of a transgenes within below ground tissues in plant species like corn.

Example 8: Crop Transformation of Genes Operably Linked to the Promoter from a *Brachypodium distachyon* Metallothionein-Like Gene (Mtl)

Soybean may be transformed with genes operably linked to the promoter from a *Brachypodium distachyon* metallothionein-like gene (mtl) by utilizing the same techniques previously described in Example #11 or Example #13 of patent application WO 2007/053482.

Cotton may be transformed with genes operably linked to the promoter from a *Brachypodium distachyon* metallothionein-like gene (mtl) by utilizing the same techniques previously described in Examples #14 of U.S. Pat. No. 7,838,733 or Example #12 of patent application WO 2007/053482 (Wright et al.).

Canola may be transformed with genes operably linked to the promoter from a *Brachypodium distachyon* metallothionein-like gene (mtl) by utilizing the same techniques previously described in Example #26 of U.S. Pat. No. 7,838,733 or Example #22 of patent application WO 2007/053482 (Wright et al.).

Wheat may be transformed with genes operably linked to the promoter from a *Brachypodium distachyon* metallothionein-like gene (mtl) by utilizing the same techniques previously described in Example #23 of patent application WO 2013/116700A1 (Lira et al.).

Rice may be transformed with genes operably linked to the promoter from a *Brachypodium distachyon* metallothionein-like gene (mtl) by utilizing the same techniques previously described in Example #19 of patent application WO 2013/116700A1 (Lira et al.).

Example 9: *Agrobacterium*-Mediated Transformation of Genes Operably Linked to the Promoter from a *Brachypodium distachyon* Metallothionein-Like Gene (Mtl)

In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5): 587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18.

The latin names for these and other plants are given below. It should be clear that other (non-*Agrobacterium*) transformation techniques can be used to transform genes operably linked to the promoter from a *Brachypodium distachyon* Metallothionein-like gene (mtl), for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa*, *Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense,* and *frutescens*), Lettuce (*Lactuca sativa, perennis,* and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*). Transformation of such plants, with genes operably linked to the promoter from a *Brachypodium distachyon* Metallothionein-like gene (mtl), for example, is contemplated in embodiments of the subject disclosure.

Use of the promoter from a *Brachypodium distachyon* Metallothionein-like gene (mtl) to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of the promoter from a *Brachypodium distachyon* Metallothionein-like gene (mtl) to drive operably linked genes can be deployed in ornamental and fruit-bearing species. Such applications are also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

SEQUENCE LISTING

```
<160> NUMBER OF SEQ ID NOS: 18

<210> SEQ ID NO 1
<211> LENGTH: 2000
<212> TYPE: DNA
<213> ORGANISM: Brachypodium distachyon

<400> SEQUENCE: 1
tttcgtgtgc ttacttgggg cttcctttgg gcctgcggaa gcagacggcg tgccagctga      60
gaccgttggt ggacaatgtg gatggacgtc tagcttcgtg gaaggccctt ctcctttcca     120
agggaggatg actggtgctg gtcaagtcca ccctgacagc gatgccggtc tactcgatga     180
tgtcactcga cctttcggac aagatcatca aagggtgga caagatctgt cgtggtttcc     240
tttggcgtgg tcagaaggac gctaaagggg ggggggcatt gtatggtggc ttgggtcgtg     300
gtgtgttcgc cgaagccttt cggtggactc ggaattccaa atcttcgcat gctcaacgag     360
gccttgaggg tccgctagag gtggcttgag agggtggacg attccaaacc atgggtcggt     420
ttcaaggttg agacgcccag aggtctatgt tatctttgag gcggccactt cctctttggt     480
gggcgatggc cggaagaccc tcttctggac cgatcgttgg ctgcatggcg tctgtttttcg     540 agatgcgttc ctgatcctcg tgggccatgt ttgccacaag tttttgcgca cgcgcacagt     600
gcgggaggct ctgcatggag cgtggactgg cgacatgggt ccagacctaa agggaagcta     660
ctcttgagga gttcctcact ctctgggact ggcttcgtgg ggtccaactg gaagaaggga     720
gggccgactc tcttcattgg aactggtctc gtggtgatag ttactcggca aagactgctt     780
atgcgaatct cttcactggc cgcatggttg acccgttagc ggctgagatc tagggcttcg     840
gagaggtgtc gtttcttcgt ctggctcgca gttcgaaata gatgctagac ggcggatcgc     900
ttgcgaggcg tgggcttccc caccctgaca agtgtcagga gatggagacc atttcccatc     960
tactcttggg gtgtgtcttg gcgaggcagg tttgggagcg cttgtgggcg gcttggggac    1020
acgtggagtg ggctccgaat gcggatgcta ctctgcggga atggtggtct tctcttcct    1080 taccacggcg agcccggagg gacttccgga cggggatcat acttgttctt tggaccattt    1140
ggtgccattg gaatgatgtg gccttccttg cagcttgtcg tgcttcgcct ccaggaggag    1200
tttggtcggt gggcgcacgc cggcctcttt aggggtagag tgtctattcc agccttgatg    1260
gtgagtggtt ggatagctag cacatagtct ttttttctct ttcttgccac ttggtgatgt    1320
```

```
tgtattgccg cttcggcgtt gtactagcct tctggctctt cttatttaat cgatgatgca   1380
cccgctgggt ggcattcttg aaattttttt gagaaaatac tcctacaaag gaagtacagt   1440
aatttgatac acaatgcttt ctctaaatac gaaaatacaa acatcctaat gttattccaa   1500
ctatgctact ccctccgttc ctaaactctt atctttgttt ttgttcaaat ttgtaccaaa   1560
caacgacaaa aatttagtaa cggaggaagt atatatacga agtgatacca aataaggtgt   1620
ttctttactt gaaagctagt tcctctgagg taaaagaaat gatgaggatc aaggaaggcc   1680
catttcttgc cggcacgcag ttgccgaagt cagtagattt aaaatgacct cacatactga   1740
agaaggaaag ggaagttaac cacgccattg ttgctttagc agaaagcaac catatcctaa   1800
ttaacatcac agtacacgtt gaaacggcag ggcacgataa ttggtgaaga ctgattccag   1860
ggagcatcgt ggcacgcaaa aacgcccttg ccttgttccc ttataaatag tggtgcagaa   1920
gatacatttg tgatcaccat ctcaaagcgc ctctttattc ccctttcatc ttgagcttaa   1980
gtactagaga aaaattaagg                                                2000
```

<210> SEQ ID NO 2
<211> LENGTH: 3340
<212> TYPE: DNA
<213> ORGANISM: Brachypodium distachyon

<400> SEQUENCE: 2

```
tttcgtgtgc ttacttgggg cttcctttgg gcctgcggaa gcagacggcg tgccagctga    60
gaccgttggt ggacaatgtg gatggacgtc tagcttcgtg gaaggcccct ctcctttcca   120
agggaggatg actggtgctg gtcaagtcca ccctgacagc gatgccggtc tactcgatga   180
tgtcactcga cctttcggac aagatcatca aagggggtgga caagatctgt cgtggttttcc   240 tttggcgtgg tcagaaggac gctaaagggg gggggcatt gtatggtggc ttgggtcgtg   300
gtgtgttcgc cgaagccttt cggtggactc ggaattccaa atcttcgcat gctcaacgag   360
gccttgaggg tccgctagag gtggcttgag agggtggacg attccaaacc atgggtcggt   420
ttcaaggttg agacgcccag aggtctatgt tatctttgag gcggccactt cctctttggt   480
gggcgatggc cggaagaccc tcttctggac cgatcgttgg ctgcatggcg tctgttttcg   540
agatgcgttc ctgatcctcg tgggccatgt ttgccacaag ttttttgcgca cgcgcacagt   600 gcggaggct ctgcatggag cgtggactgg cgacatgggt ccagacctaa agggaagcta   660
ctcttgagga gttcctcact ctctgggact ggcttcgtgg ggtccaactg gaagaaggga   720
gggccgactc tcttcattgg aactggtctc gtggtgatag ttactcggca aagactgctt   780
atgcgaatct cttcactggc cgcatggttg accgttagc ggctgagatc tagggcttcg   840
gagaggtgtc gtttcttcgt ctggctcgca gttcgaaata gatgctagac ggcggatcgc   900
ttgcgaggcg tgggcttccc caccctgaca agtgtcagga gatggagacc atttcccatc   960
tactcttggg gtgtgtcttg gcgaggcagg tttgggagcg cttgtgggcg gcttggggac  1020
acgtggagtg ggctccgaat gcggatgcta ctctgcggga atggtggtct tctcttccct  1080
taccacggcg agcccggagg gacttccgga cggggatcat acttgttctt tggaccattt  1140
ggtgccattg gaatgatgtg gccttccttg cagcttgtcg tgcttcgcct ccaggaggag  1200
tttggtcggt gggcgcacgc cggcctcttt aggggtagag tgtctattcc agccttgatg  1260
gtgagtggtt ggatagctag cacatagtct ttttttctct ttcttgccac ttggtgatgt  1320
tgtattgccg cttcggcgtt gtactagcct tctggctctt cttatttaat cgatgatgca  1380
cccgctgggt ggcattcttg aaattttttt gagaaaatac tcctacaaag gaagtacagt  1440
```

```
aatttgatac acaatgcttt ctctaaatac gaaaatacaa acatcctaat gttattccaa    1500
ctatgctact ccctccgttc ctaaactctt atctttgttt ttgttcaaat ttgtaccaaa    1560
caacgacaaa aatttagtaa cggaggaagt atatatacga agtgatacca aataaggtgt    1620
ttctttactt gaaagctagt tcctctgagg taaaagaaat gatgaggatc aaggaaggcc    1680
catttcttgc cggcacgcag ttgccgaagt cagtagattt aaaatgacct cacatactga    1740
agaaggaaag ggaagttaac cacgccattg ttgctttagc agaaagcaac catatcctaa    1800
ttaacatcac agtacacgtt gaaacggcag ggcacgataa ttggtgaaga ctgattccag    1860
ggagcatcgt ggcacgcaaa aacgcccttg ccttgttccc ttataaatag tggtgcagaa    1920
gatacatttg tgatcaccat ctcaaagcgc ctctttattc cccttcatc ttgagcttaa     1980 gtactagaga aaaattaagg atgtcttgca gctgtggatc tggatgcagc tgcggctcaa    2040
actgcacctg cgggtatgta tagatgctta attctgtgtt gcagattact acgtagctgc    2100
taataccatc taagtaatga caatgctttc tcatgatgat caattttcat ttgctgtgtg    2160
gttcagcaag atgtaccctg acttggcaga gaagagcggc ggcacccagc aggccaccac    2220
catgatcctc ggcgttgcgc ctgctaaggc ccagtttgag gaggccgccg agtccggtga    2280
ggccggccat ggctgcagct gcggcgccaa ctgcaagtgc gacccgtgca actgctaaga    2340
tgcacgcgac gcgctgctgc ttgtggtgtg tgtttgtgtg atctcgactg aataaaaggg    2400
acacggtaca tccgggggttg gttggtgctc gagtcgagtg tgcaaggttg tgtggtttgc    2460
cagctcttgg tgtgtgtctc cttgtgctca tgtgacttgt gaaaccatta atagtaacca    2520
ctttgtgctt gtgtgtgtgt gggcacctgt gttctgtaa tggtctatct ggagtgaata     2580
tatacaagac aggtttgcct aaccatgcct tttccttcct tgaggtcatc gcgccaacac    2640
gaatgacgag aaccaatgat cttaggacta tcaaatagac aatataactc agcatggagc    2700
aatgtactgc taatgaacgg tcctaatcaa tacagttggg aagcagtaat cgatggaaaa    2760
cacttcctca gttcagaagg gaacatgtag atgggaaagt aaacaggata tatagacaca    2820
tgcagttagg tctaccacaa gaagacatgc cacaggacta aaaacagaag ctgggtttgg    2880
aacaacttat gcagacgcta gctatccaga taaaccttag agaaacagct atgagaataa    2940
gcgtctgaaa tttgtagttg cctgtttgga atggcttatg gacgacaagc ttattttctg    3000
gagtagccta caagtacaag ccaaggcaca tgctgttcca aactggccca tattttgcac    3060
aaccaaagga aaagagacag tgacataaga gcatctccag tgattcagtg agataccccca   3120 aagtcatcca aatgtccgtt tcggccgaaa tggacatgct ggccagaaaa acatctccca    3180
atgggttacc ccaaatagat attttgtatg ttttgtccgg cccaatcccc aaacatctcc    3240
taaatttggg gcaactttgc ggtgtccagt gtccggtgtc cgggcccact tctttttctc    3300
ccaagcgagc atcttcctcc cgaagcacga agccccccgtc                          3340
```

<210> SEQ ID NO 3
<211> LENGTH: 1002
<212> TYPE: DNA
<213> ORGANISM: Brachypodium distachyon

<400> SEQUENCE: 3

```
gatgcacgcg acgcgctgct gcttgtggtg tgtgtttgtg tgatctcgac tgaataaaag     60
ggacacggta catccggggt tggttggtgc tcgagtcgag tgtgcaaggt tgtgtggttt    120
gccagctctt ggtgtgtgtc tccttgtgct catgtgactt gtgaaaccat taatagtaac    180
```

| | |
|---|---|
| cactttgtgc ttgtgtgtgt gtgggcacct gtgtttctgt aatggtctat ctggagtgaa | 240 |
| tatatacaag acaggtttgc ctaaccatgc cttttccttc cttgaggtca tcgcgccaac | 300 |
| acgaatgacg agaaccaatg atcttaggac tatcaaatag acaatataac tcagcatgga | 360 |
| gcaatgtact gctaatgaac ggtcctaatc aatacagttg ggaagcagta atcgatggaa | 420 |
| aacacttcct cagttcagaa gggaacatgt agatgggaaa gtaaacagga tatatagaca | 480 |
| catgcagtta ggtctaccac aagaagacat gccacaggac taaaaacaga agctgggttt | 540 |
| ggaacaactt atgcagacgc tagctatcca gataaacctt agagaaacag ctatgagaat | 600 |
| aagcgtctga aatttgtagt tgcctgtttg aatggcttaa tggacgacaa gcttattttc | 660 |
| tggagtagcc tacaagtaca agccaaggca catgctgttc caaactggcc catattttgc | 720 |
| acaaccaaag gaaagagac agtgacataa gagcatctcc agtgattcag tgagataccc | 780 |
| caaagtcatc caaatgtccg tttcggccga aatggacatg ctggccagaa aaacatctcc | 840 |
| caatgggtta ccccaaatag atattttgta tgttttgtcc ggcccaatcc ccaaacatct | 900 |
| cctaaatttg gggcaacttt gcggtgtcca gtgtccggtg tccggcccca cttcttttc | 960 |
| tcccaagcga gcatcttcct cccgaagcac gaagccccg tc | 1002 |

<210> SEQ ID NO 4
<211> LENGTH: 3934
<212> TYPE: DNA
<213> ORGANISM: Artificial Sequence
<220> FEATURE:
<223> OTHER INFORMATION: phi-yfp gene expression cassette; where the
      promoter of SEQ ID NO:1 and the 3'UTR of SEQ ID NO:3 drive the
      phi-yfp gene.

<400> SEQUENCE: 4

| | |
|---|---|
| tttcgtgtgc ttacttgggg cttcctttgg gcctgcggaa gcagacggcg tgccagctga | 60 |
| gaccgttggt ggacaatgtg gatggacgtc tagcttcgtg gaaggcccctt ctcctttcca | 120 |
| agggaggatg actggtgctg gtcaagtcca ccctgacagc gatgccggtc tactcgatga | 180 |
| tgtcactcga cctttcggac aagatcatca aggggtggaa caagatctgt cgtggtttcc | 240 |
| tttggcgtgg tcagaaggac gctaaagggg gggggcatt gtatggtggc ttgggtcgtg | 300 |
| gtgtgttcgc cgaagccttt cggtggactc ggaattccaa atcttcgcat gctcaacgag | 360 |
| gccttgaggg tccgctagag gtggcttgag agggtggacg attccaaacc atgggtcggt | 420 |
| ttcaaggttg agacgcccag aggtctatgt tatctttgag gcggccactt cctctttggt | 480 |
| gggcgatggc cggaagaccc tcttctggac cgatcgttgg ctgcatggcg tctgttttcg | 540 |
| agatgcgttc ctgatcctcg tgggccatgt ttgccacaag ttttttgcgca cgcgcacagt | 600 |
| gcgggaggct ctgcatggag cgtggactgg cgacatgggt ccagacctaa agggaagcta | 660 |
| ctcttgagga gttcctcact ctctgggact ggcttcgtgg ggtccaactg gaagaaggga | 720 |
| gggccgactc tcttcattgg aactggtctc gtggtgatag ttactcggca aagactgctt | 780 |
| atgcgaatct cttcactggc cgcatggttg acccgttagc ggctgagatc tagggcttcg | 840 |
| gagaggtgtc gtttcttcgt ctggctcgca gttcgaaata gatgctagac ggcggatcgc | 900 |
| ttgcgaggcg tgggcttccc caccctgaca agtgtcagga gatggagacc atttcccatc | 960 |
| tactcttggg gtgtgtcttg gcgaggcagg tttgggagcg cttgtgggcg gcttggggac | 1020 |
| acgtggagtg ggctccgaat gcggatgcta ctctgcggga atggtggtct tctcttccct | 1080 |
| taccacggca gcccggagg gacttccgga cggggatcat acttgttctt ggaccatttt | 1140 |
| ggtgccattg gaatgatgtg gccttccttg cagcttgtcg tgcttcgcct ccaggaggag | 1200 |

```
tttggtcggt gggcgcacgc cggcctcttt aggggtagag tgtctattcc agccttgatg   1260
gtgagtggtt ggatagctag cacatagtct ttttttctct ttcttgccac ttggtgatgt   1320
tgtattgccg cttcggcgtt gtactagcct tctggctctt cttatttaat cgatgatgca   1380
cccgctgggt ggcattcttg aaattttttt gagaaaatac tcctacaaag gaagtacagt   1440
aatttgatac acaatgcttt ctctaaatac gaaaatacaa acatcctaat gttattccaa   1500
ctatgctact ccctccgttc ctaaactctt atctttgttt ttgttcaaat ttgtaccaaa   1560
caacgacaaa aatttagtaa cggaggaagt atatatacga agtgatacca ataaggtgt    1620 ttctttactt gaaagctagt tcctctgagg taaaagaaat gatgaggatc aaggaaggcc   1680
catttcttgc cggcacgcag ttgccgaagt cagtagattt aaaatgacct cacatactga   1740
agaaggaaag ggaagttaac cacgccattg ttgctttagc agaaagcaac catatcctaa   1800
ttaacatcac agtacacgtt gaaacggcag ggcacgataa ttggtgaaga ctgattccag   1860
ggagcatcgt ggcacgcaaa aacgcccttg ccttgttccc ttataaatag tggtgcagaa   1920
gatacatttg tgatcaccat ctcaaagcgc ctctttattc ccctttcatc ttgagcttaa   1980
gtactagaga aaaattaagg ccagaagaca ccatgtcatc tggagcactt ctctttcatg   2040
ggaagattcc ttacgttgtg gagatggaag ggaatgttga tggccacacc tttagcatac   2100
gtgggaaagg ctacggagat gcctcagtgg gaaaggtatg tttctgcttc tacctttgat   2160
atatatataa taattatcac taattagtag taatatagta tttcaagtat ttttttcaaa   2220
ataaaagaat gtagtatata gctattgctt ttctgtagtt tataagtgtg tatattttaa   2280
tttataactt ttctaatata tgaccaaaac atggtgatgt gcaggttgat gcacaattca   2340
tctgtactac cggagatgtt cctgtgcctt ggagcacact tgtcaccact ctcacctatg   2400
gagcacagtg ctttgccaag tatggtccag agttgaagga cttctacaag tcctgtatgc   2460
cagatggcta tgtgcaagag cgcacaatca cctttgaagg agatggcaac ttcaagacta   2520
gggctgaagt caccttttgag aatgggtctg tctacaatag ggtcaaactc aatggtcaag   2580
gcttcaagaa agatggtcac gtgttgggaa agaacttgga gttcaacttc actccccact   2640
gcctctacat ctggggagac caagccaacc acggtctcaa gtcagccttc aagatatgtc   2700
atgagattac tggcagcaaa ggcgacttca tagtggctga ccacacccag atgaacactc   2760
ccattggtgg aggtccagtt catgttccag agtatcatca tatgtcttac catgtgaaac   2820
tttccaaaga tgtgacagac cacagagaca acatgagctt gaaagaaact gtcagagctg   2880
ttgactgtcg caagacctac ctttgagtag ttagcttaat cacctagagc tcgatgcacg   2940
cgacgcgctg ctgcttgtgg tgtgtgtttg tgtgatctcg actgaataaa agggacacgg   3000
tacatccggg gttggttggt gctcgagtcg agtgtgcaag gttgtgtggt ttgccagctc   3060
ttggtgtgtg tctccttgtg ctcatgtgac ttgtgaaacc attaatagta accactttgt   3120
gcttgtgtgt gtgtgggcac ctgtgtttct gtaatggtct atctgagtg aatatataca    3180 agacaggttt gcctaaccat gccttttcct tccttgaggt catcgcgcca acacgaatga   3240
cgagaaccaa tgatcttagg actatcaaat agacaatata actcagcatg gagcaatgta   3300
ctgctaatga acggtcctaa tcaatacagt tgggaagcag taatcgatgg aaaacacttc   3360
ctcagttcag aagggaacat gtagatggga aagtaaacag gatatataga cacatgcagt   3420
taggtctacc acaagaagac atgccacagg actaaaaaca gaagctgggt ttggaacaac   3480
ttatgcagac gctagctatc cagataaacc ttagagaaac agctatgaga ataagcgtct   3540
```

```
gaaatttgta gttgcctgtt tggaatggct tatggacgac aagcttattt tctggagtag    3600
cctacaagta caagccaagg cacatgctgt tccaaactgg cccatatttt gcacaaccaa    3660
aggaaaagag acagtgacat aagagcatct ccagtgattc agtgagatac cccaaagtca    3720
tccaaatgtc cgtttcggcc gaaatggaca tgctggccag aaaaacatct cccaatgggt    3780
taccccaaat agatattttg tatgttttgt ccggcccaat ccccaaacat ctcctaaatt    3840
tggggcaact ttgcggtgtc cagtgtccgg tgtccgggcc cacttctttt tctcccaagc    3900
gagcatcttc ctcccgaagc acgaagcccc cgtc                               3934

<210> SEQ ID NO 5
<211> LENGTH: 3307
<212> TYPE: DNA
<213> ORGANISM: artificial sequence
<220> FEATURE:
<223> OTHER INFORMATION: aad-1 selectable marker gene expression
      cassette that contains the Zea mays Ubiquitin 1 promoter and the
      Zea mays Lipase 3'UTR

<400> SEQUENCE: 5
gtgcagcgtg acccggtcgt gcccctctct agagataatg agcattgcat gtctaagtta      60
taaaaaatta ccacatattt ttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc ttttttttg      300 caaatagctt cacctatata atacttcatc catttttatta gtacatccat ttagggttta   360
gggttaatgg tttttataga ctaattttttt tagtacatct attttattct atttttagcct  420 ctaaattaag aaaactaaaa ctctatttta gttttttttat ttaatagttt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca     660
cggcatctct gtcgctgcct ctggaccccct ctcgagagtt ccgctccacc gttggacttg    720
ctccgctgtc ggcatccaga aattgcgtgg cggagcggca gacgtgagcc ggcacggcag     780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccaccgcgt    960 cggcacctcc gcttcaaggt acgccgctcg tcctccccccc cccccccct ctctacttc    1020 tctagatcgg cgttccggtc catgcatggt tagggcccgg tagttctact tctgttcatg    1080
tttgtgttag atccgtgttt gtgttagatc cgtgctgcta gcgttcgtac acggatgcga    1140
cctgtacgtc agacacgttc tgattgctaa cttgccagtg tttctctttg gggaatcctg    1200
ggatggctct agccgttccg cagacgggat cgatttcatg atttttttg tttcgttgca     1260 tagggtttgg tttgcccttt tcctttattt caatatatgc cgtgcacttg tttgtcgggt   1320
catcttttca tgcttttttt tgtcttggtt gtgatgatgt ggtctggttg ggcggtcgtt    1380
ctagatcgga gtagaattct gtttcaaact acctggtgga tttattaatt ttggatctgt    1440
atgtgtgtgc catacatatt catagttacg aattgaagat gatggatgga aatatcgatc    1500
taggataggt atacatgttg atgcgggttt tactgatgca tatacagaga tgcttttttgt   1560 tcgcttggtt gtgatgatgt ggtgtggttg ggcggtcgtt cattcgttct agatcggagt    1620
```

```
agaatactgt tcaaactac ctggtgtatt tattaatttt ggaactgtat gtgtgtgtca      1680
tacatcttca tagttacgag tttaagatgg atggaaatat cgatctagga taggtataca      1740
tgttgatgtg ggttttactg atgcatatac atgatggcat atgcagcatc tattcatatg      1800
ctctaacctt gagtacctat ctattataat aaacaagtat gttttataat tatttcgatc      1860
ttgatatact tggatgatgg catatgcagc agctatatgt ggatttttt agccctgcct        1920
tcatacgcta tttatttgct tggtactgtt cttttgtcg atgctcaccc tgttgtttgg        1980
tgttacttct gcaggtacag tagttagttg aggtaccgga tccacacgac accatggctc      2040
atgctgccct cagccctctc tcccaacgct tgagagaat agctgtccag ccactcactg        2100
gtgtccttgg tgctgagatc actggagtgg acttgaggga accacttgat gacagcacct      2160
ggaatgagat attggatgcc ttccacactt accaagtcat ctactttcct ggccaagcaa      2220
tcaccaatga gcagcacatt gcattctcaa gaaggtttgg accagttgat ccagtgcctc      2280
ttctcaagag cattgaaggc tatccagagg ttcagatgat ccgcagagaa gccaatgagt      2340
ctggaagggt gattggtgat gactggcaca cagactccac tttccttgat gcacctccag      2400
ctgctgttgt gatgagggcc atagatgttc ctgagcatgg cggagacact gggttccttt      2460
caatgtacac agcttgggag accttgtctc caaccatgca agccaccatc gaagggctca      2520
acgttgtgca ctctgccaca cgtgtgttcg gttccctcta ccaagcacag aaccgtcgct      2580
tcagcaacac ctcagtcaag gtgatggatg ttgatgctgg tgacagagag acagtccatc      2640
ccttggttgt gactcatcct ggctctggaa ggaaaggcct ttatgtgaat caagtctact      2700
gtcagagaat tgagggcatg acagatgcag aatcaaagcc attgcttcag ttcctctatg      2760
agcatgccac cagatttgac ttcacttgcc gtgtgaggtg gaagaaagac caagtccttg      2820
tctgggacaa cttgtgcacc atgcaccgtg ctgttcctga ctatgctggc aagttcagat      2880
acttgactcg caccacagtt ggtggagtta ggcctgcccg ctgagtagtt agcttaatca      2940
cctagagctc ggtcgcagcg tgtgcgtgtc cgtcgtacgt tctggccggc cgggccttgg      3000
gcgcgcgatc agaagcgttg cgttggcgtg tgtgtgcttc tggtttgctt taattttacc      3060
aagtttgttt caaggtggat cgcgtggtca aggcccgtgt gctttaaaga cccaccggca      3120
ctggcagtga tgttgctgc ttgtgtaggc tttggtacgt atgggcttta tttgcttctg        3180
gatgttgtgt actacttggg tttgttgaat tattatgagc agttgcgtat tgtaattcag      3240
ctgggctacc tggacattgt tatgtattaa taaatgcttt gctttcttct aaagatcttt      3300
aagtgct                                                                3307
```

<210> SEQ ID NO 6
<211> LENGTH: 338
<212> TYPE: DNA
<213> ORGANISM: Brachypodium distachyon

<400> SEQUENCE: 6

```
atgtcttgca gctgtggatc tggatgcagc tgcggctcaa actgcacctg cgggtatgta       60
tagatgctta attctgtgtt gcagattact acgtagctgc taataccatc taagtaatga      120
caatgctttc tcatgatgat caattttcat ttgctgtgtg gttcagcaag atgtaccctg      180
acttggcaga gaagagcggc ggcacccagc aggccaccac catgatcctc ggcgttgcgc      240
ctgctaaggc ccagtttgag gaggccgccg agtccggtga ggccggccat ggctgcagct      300
gcggcgccaa ctgcaagtgc gacccgtgca actgctaa                              338
```

<210> SEQ ID NO 7
<211> LENGTH: 1730
<212> TYPE: DNA
<213> ORGANISM: Brachypodium distachyon

<400> SEQUENCE: 7

| | | |
|---|---|---|
| gggggggcatt gtatggtggc ttgggtcgtg gtgtgttcgc cgaagccttt cggtggactc | 60 |
| ggaattccaa atcttcgcat gctcaacgag gccttgaggg tccgctagag gtggcttgag | 120 |
| agggtggacg attccaaacc atgggtcggt ttcaaggttg agacgcccag aggtctatgt | 180 |
| tatctttgag gcggccactt cctctttggt gggcgatggc cggaagaccc tcttctggac | 240 |
| cgatcgttgg ctgcatggcg tctgttttcg agatgcgttc ctgatcctcg tgggccatgt | 300 |
| ttgccacaag ttttttgcgca cgcgcacagt gcgggaggct ctgcatggag cgtggactgg | 360 |
| cgacatgggt ccagacctaa aggaagcta ctcttgagga gttcctcact ctctgggact | 420 |
| ggcttcgtgg ggtccaactg gaagaaggga gggccgactc tcttcattgg aactggtctc | 480 |
| gtggtgatag ttactcggca aagactgctt atgcgaatct cttcactggc cgcatggttg | 540 |
| acccgttagc ggctgagatc tagggcttcg gagaggtgtc gtttcttcgt ctggctcgca | 600 |
| gttcgaaata gatgctagac ggcggatcgc ttgcgaggcg tgggcttccc caccctgaca | 660 |
| agtgtcagga gatggagacc atttcccatc tactcttggg gtgtgtcttg gcgaggcagg | 720 |
| tttgggagcg cttgtgggcg gcttggggac acgtggagtg ggctccgaat gcggatgcta | 780 |
| ctctgcggga atggtggtct tctcttccct taccacggcg agcccggagg gacttccgga | 840 |
| cggggatcat acttgttctt tggaccattt ggtgccattg gaatgatgtg gccttccttg | 900 |
| cagcttgtcg tgcttcgcct ccaggaggag tttggtcggt gggcgcacgc cggcctcttt | 960 |
| aggggtagag tgtctattcc agccttgatg gtgagtggtt ggatagctag cacatagtct | 1020 |
| ttttttctct ttcttgccac ttggtgatgt tgtattgccg cttcggcgtt gtactagcct | 1080 |
| tctggctctt cttatttaat cgatgatgca cccgctgggt ggcattcttg aaattttttt | 1140 |
| gagaaaatac tcctacaaag gaagtacagt aatttgatac acaatgcttt ctctaaatac | 1200 |
| gaaaatacaa acatcctaat gttattccaa ctatgctact ccctccgttc ctaaactctt | 1260 |
| atctttgttt tgttcaaat ttgtaccaaa caacgacaaa aatttagtaa cggaggaagt | 1320 |
| atatatacga agtgatacca aataaggtgt ttctttactt gaaagctagt tcctctgagg | 1380 |
| taaaagaaat gatgaggatc aaggaaggcc catttcttgc cggcacgcag ttgccgaagt | 1440 |
| cagtagattt aaaatgacct cacatactga agaaggaaag ggaagttaac cacgccattg | 1500 |
| ttgctttagc agaaagcaac catatcctaa ttaacatcac agtacacgtt gaaacggcag | 1560 |
| ggcacgataa ttggtgaaga ctgattccag ggagcatcgt ggcacgcaaa aacgcccttg | 1620 |
| ccttgttccc ttataaatag tggtgcagaa gatacatttg tgatcaccat ctcaaagcgc | 1680 |
| ctctttattc ccctttcatc ttgagcttaa gtactagaga aaaattaagg | 1730 |

<210> SEQ ID NO 8
<211> LENGTH: 1530
<212> TYPE: DNA
<213> ORGANISM: Brachypodium distachyon

<400> SEQUENCE: 8

| | | |
|---|---|---|
| cctctttggt gggcgatggc cggaagaccc tcttctggac cgatcgttgg ctgcatggcg | 60 |
| tctgttttcg agatgcgttc ctgatcctcg tgggccatgt ttgccacaag ttttttgcgca | 120 |
| cgcgcacagt gcgggaggct ctgcatggag cgtggactgg cgacatgggt ccagacctaa | 180 |

```
agggaagcta ctcttgagga gttcctcact ctctgggact ggcttcgtgg ggtccaactg     240
gaagaaggga gggccgactc tcttcattgg aactggtctc gtggtgatag ttactcggca     300
aagactgctt atgcgaatct cttcactggc cgcatggttg acccgttagc ggctgagatc     360
tagggcttcg gagaggtgtc gtttcttcgt ctggctcgca gttcgaaata gatgctagac     420
ggcggatcgc ttgcgaggcg tgggcttccc caccctgaca agtgtcagga gatggagacc     480
atttcccatc tactcttggg gtgtgtcttg gcgaggcagg tttgggagcg cttgtgggcg     540
gcttggggac acgtggagtg ggctccgaat gcggatgcta ctctgcggga atggtggtct     600
tctcttccct taccacggcg agcccggagg gacttccgga cggggatcat acttgttctt     660
tggaccattt ggtgccattg aatgatgtg gccttccttg cagcttgtcg tgcttcgcct     720
ccaggaggag tttggtcggt gggcgcacgc cggcctcttt aggggtagag tgtctattcc     780
agccttgatg gtgagtggtt ggatagctag cacatagtct tttttctct ttcttgccac     840 ttggtgatgt tgtattgccg cttcggcgtt gtactagcct tctggctctt cttatttaat     900
cgatgatgca cccgctgggt ggcattcttg aaatttttt gagaaaatac tcctacaaag     960
gaagtacagt aatttgatac acaatgcttt ctctaaatac gaaatacaa acatcctaat    1020 gttattccaa ctatgctact ccctccgttc ctaaactctt atctttgttt ttgttcaaat    1080
ttgtaccaaa caacgacaaa aatttagtaa cggaggaagt atatatacga agtgatacca    1140
aataaggtgt ttctttactt gaaagctagt tcctctgagg taaagaaat gatgaggatc    1200 aaggaaggcc catttcttgc cggcacgcag ttgccgaagt cagtagattt aaaatgacct    1260
cacatactga agaaggaaag ggaagttaac cacgccattg ttgctttagc agaaagcaac    1320
catatcctaa ttaacatcac agtacacgtt gaaacggcag gcacgataa ttggtgaaga    1380 ctgattccag ggagcatcgt ggcacgcaaa acgcccttg ccttgttccc ttataaatag    1440
tggtgcagaa gatacatttg tgatcaccat ctcaaagcgc tctttattc ccctttcatc    1500 ttgagcttaa gtactagaga aaaattaagg                                     1530

<210> SEQ ID NO 9
<211> LENGTH: 1330
<212> TYPE: DNA
<213> ORGANISM: Brachypodium distachyon

<400> SEQUENCE: 9
gttcctcact ctctgggact ggcttcgtgg ggtccaactg gaagaaggga gggccgactc      60
tcttcattgg aactggtctc gtggtgatag ttactcggca aagactgctt atgcgaatct     120
cttcactggc cgcatggttg acccgttagc ggctgagatc tagggcttcg gagaggtgtc     180
gtttcttcgt ctggctcgca gttcgaaata gatgctagac ggcggatcgc ttgcgaggcg     240
tgggcttccc caccctgaca agtgtcagga gatggagacc atttcccatc tactcttggg     300
gtgtgtcttg gcgaggcagg tttgggagcg cttgtgggcg gcttggggac acgtggagtg     360
ggctccgaat gcggatgcta ctctgcggga atggtggtct tctcttccct taccacggcg     420
agcccggagg gacttccgga cggggatcat acttgttctt tggaccattt ggtgccattg     480
gaatgatgtg gccttccttg cagcttgtcg tgcttcgcct ccaggaggag tttggtcggt     540
gggcgcacgc cggcctcttt aggggtagag tgtctattcc agccttgatg gtgagtggtt     600
ggatagctag cacatagtct tttttctct ttcttgccac ttggtgatgt tgtattgccg     660
cttcggcgtt gtactagcct tctggctctt cttatttaat cgatgatgca cccgctgggt     720
```

```
ggcattcttg aaattttttt gagaaaatac tcctacaaag gaagtacagt aatttgatac      780
acaatgcttt ctctaaatac gaaaatacaa acatcctaat gttattccaa ctatgctact      840
ccctccgttc ctaaactctt atctttgttt ttgttcaaat ttgtaccaaa caacgacaaa      900
aatttagtaa cggaggaagt atatatacga agtgatacca ataaggtgt ttctttactt       960 gaaagctagt tcctctgagg taaaagaaat gatgaggatc aaggaaggcc catttcttgc     1020
cggcacgcag ttgccgaagt cagtagattt aaaatgacct cacatactga agaaggaaag     1080
ggaagttaac cacgccattg ttgctttagc agaaagcaac catatcctaa ttaacatcac     1140
agtacacgtt gaaacggcag ggcacgataa ttggtgaaga ctgattccag ggagcatcgt     1200
ggcacgcaaa aacgcccttg ccttgttccc ttataaatag tggtgcagaa gatacatttg     1260
tgatcaccat ctcaaagcgc ctctttattc cctttcatc ttgagcttaa gtactagaga      1320
aaaattaagg                                                            1330

<210> SEQ ID NO 10
<211> LENGTH: 1130
<212> TYPE: DNA
<213> ORGANISM: Brachypodium distachyon

<400> SEQUENCE: 10
gttcgaaata gatgctagac ggcggatcgc ttgcgaggcg tgggcttccc caccctgaca       60
agtgtcagga gatggagacc atttcccatc tactcttggg gtgtgtcttg gcgaggcagg      120
tttgggagcg cttgtgggcg gcttgggac acgtggagtg ggctccgaat gcggatgcta       180
ctctgcggga atggtggtct tctcttccct taccacggcg agcccggagg gacttccgga      240
cggggatcat acttgttctt tggaccattt ggtgccattg aatgatgtg gccttccttg       300 cagcttgtcg tgcttcgcct ccaggaggag tttggtcggt gggcgcacgc cggcctcttt      360
aggggtagag tgtctattcc agccttgatg gtgagtggtt ggatagctag cacatagtct      420
ttttttctct ttcttgccac ttggtgatgt tgtattgccg cttcggcgtt gtactagcct      480
tctggctctt cttatttaat cgatgatgca cccgctgggt ggcattcttg aaattttttt      540
gagaaaatac tcctacaaag gaagtacagt aatttgatac acaatgcttt ctctaaatac      600
gaaaatacaa acatcctaat gttattccaa ctatgctact ccctccgttc ctaaactctt      660
atctttgttt ttgttcaaat ttgtaccaaa caacgacaaa aatttagtaa cggaggaagt      720
atatatacga agtgatacca ataaggtgt ttctttactt gaaagctagt tcctctgagg       780
taaaagaaat gatgaggatc aaggaaggcc catttcttgc cggcacgcag ttgccgaagt      840
cagtagattt aaaatgacct cacatactga agaaggaaag ggaagttaac cacgccattg      900
ttgctttagc agaaagcaac catatcctaa ttaacatcac agtacacgtt gaaacggcag      960
ggcacgataa ttggtgaaga ctgattccag ggagcatcgt ggcacgcaaa aacgcccttg     1020
ccttgttccc ttataaatag tggtgcagaa gatacatttg tgatcaccat ctcaaagcgc     1080
ctctttattc cctttcatc ttgagcttaa gtactagaga aaaattaagg                 1130

<210> SEQ ID NO 11
<211> LENGTH: 1001
<212> TYPE: DNA
<213> ORGANISM: Brachypodium distachyon

<400> SEQUENCE: 11
gcttgtgggc ggcttgggga cacgtggagt gggctccgaa tgcggatgct actctgcggg       60
aatggtggtc ttctcttccc ttaccacggc gagcccggag ggacttccgg acggggatca      120
```

```
tacttgttct ttggaccatt tggtgccatt ggaatgatgt ggccttcctt gcagcttgtc      180
gtgcttcgcc tccaggagga gtttggtcgg tgggcgcacg ccggcctctt tagggggtaga     240 gtgtctattc cagccttgat ggtgagtggt tggatagcta gcacatagtc ttttttctc      300 tttcttgcca cttggtgatg ttgtattgcc gcttcggcgt tgtactagcc ttctggctct      360
tcttatttaa tcgatgatgc acccgctggg tggcattctt gaatttttt tgagaaaata      420 ctcctacaaa ggaagtacag taatttgata cacaatgctt tctctaaata cgaaaataca     480
aacatcctaa tgttattcca actatgctac tccctccgtt cctaaactct tatctttgtt     540
tttgttcaaa tttgtaccaa acaacgacaa aaatttagta acggaggaag tatatatacg     600
aagtgatacc aaataaggtg tttctttact tgaaagctag ttcctctgag gtaaaagaaa     660
tgatgaggat caaggaaggc ccatttcttg ccggcacgca gttgccgaag tcagtagatt     720
taaaatgacc tcacatactg aagaaggaaa gggaagttaa ccacgccatt gttgctttag     780
cagaaagcaa ccatatccta attaacatca cagtacacgt tgaaacggca gggcacgata     840
attggtgaag actgattcca gggagcatcg tggcacgcaa aaacgcccctt gccttgttcc     900 cttataaata gtggtgcaga agatacattt gtgatcacca tctcaaagcg cctctttatt     960 ccccttttcat cttgagctta agtactagag aaaaattaag g                       1001

<210> SEQ ID NO 12
<211> LENGTH: 2000
<212> TYPE: DNA
<213> ORGANISM: Artificial Sequence
<220> FEATURE:
<223> OTHER INFORMATION: Modified version of a Brachypodium distachyon
      metallothionein-like gene (mtl) promoter

<400> SEQUENCE: 12
tttcgtgtgc ttacttgggg cttcctttgg gcctgcggaa gcagacggcg tgccaggtac      60
gaggttgttg gtggacaatg tggatggacg atttctagct tcgtggaagg cccttctcct     120
taagggagga tgactggtgc tggtcaagtc caccctgaca gcgatgccgg tctactcgat     180
gatgtcactc gacctttcgg acaagatcat caaaggggtg gacaaggtat gtcgtggttt     240
cctttggcgt ggtcagaagg acgctaaagg gggggggca ttgtatggtg gcttgggtcg      300
tggtgtgttc gccgaccgct ttcggtggac tcggcgtttc caaatcttcg catcctccca     360
gccttgaggg tccgctagag gtggcttgag agggtggacg attccaaacc cgatggtcgg    420
tttcaaggtt gagacgccca gaggtctatg ttatctttga ggcggccact tcctctttgg     480
tgggcgatgg ccggacgttt ccctcttctg gaccgattgt tggctgcatg gcgtctgttt     540
tcgagatgcg ttcctgatcc tcgtgggcca tgtttgccac aagttttgc ttacgcgcac      600 agtgcgggag gctctgcatg gagcgtggac tggcgacatg ggtccagacc taagggaag    660 ctactcttga ggacttcact ctctgggact ggcttcgtgg ggtccaactg gaagaaggga     720
gggccgactc tcttcattgg aactggtgtg gtggtgatag ttactcggca agactgctt      780 atgcgaatct tcactggccg catggttgac ccgttagcgg ctgagagtta gggcttcgga     840
gaggtgtcgt tcttcgtct ggctcgcagt tcttgaaata gatgctagac ggcggatcgc      900
ttgcgaggcg tgggcttccc caccctgaca agtgtcagga gatggagtcg atttcccatc     960
tactcttggg gtgtgtcttg gcgaggcagg tttgggagcg cttgtgggcg gcttggggac    1020
acgtggagtg ggctccgaat gcggatgcta ctctgcggga atggtggtct ttctcttccc    1080
ttaccacggc gagcccggag ggacttccgg acggggatca tacttgttct ttggaccatt    1140
```

```
tggtgccatt ggaatgatgt ggccttcctt gcagcttgtc gtgcttcgcc tggaggaatt    1200
gtttggtcgg tgggcgcacg ccggcctctt taggggtaga gtgtctattc cagccttgat    1260
ggtgagtggt tggatagcta gcacatagtc ttttttttctc tttcttgcca cttggtgatg    1320
ttgtattgcc gcttcggcgt tgtactagcc ttctggctct tcttatttaa tgatgatgca    1380
cccgctgggt ggcattcttg aaattttttt gagaaaatac tcctacaaag gaagtacagt    1440
aatttgatac acaatgcttt ctctaaatac gaaaatacaa acatcctaat gttattccaa    1500
ctatgctact ccctccgttc ctaaactctt atctttgttt ttgttcaaat ttgtaccaaa    1560
caacgacaaa aatttagtaa cggaggaagt atatatacga agtgatacca ataaggtgt     1620 ttctttactt gaaagctagt tcctctgagg taaagaaat gatgaggatc aaggaaggcc     1680
catttcttgc cggcacgcag ttgccgaagt cagtagattt aaaatgacct cacatactga    1740
agaaggaaag ggaagttaac cacgccattg ttgctttagc agaaagcaac catatcctaa    1800
ttaacatcac agtacacgtt gaaacggcag ggcacgataa ttggtgaaga ctgattccag    1860
ggagcatcgt ggcacgcaaa aacgcccttg ccttgttccc ttataaatag tggtgcagaa    1920
gatacatttg tgatcaccat ctcaaagcgc ctctttattc ccctttcatc ttgagcttaa    1980
gtactagaga aaaattaagg                                                 2000
```

```
<210> SEQ ID NO 13
<211> LENGTH: 264
<212> TYPE: DNA
<213> ORGANISM: Brachypodium distachyon

<400> SEQUENCE: 13
gatgcacgcg acgcgctgct gcttgtggtg tgtgtttgtg tgatctcgac tgaataaaag     60
ggacacggta catccggggt tggttggtgc tcgagtcgag tgtgcaaggt tgtgtggttt    120
gccagctctt ggtgtgtgtc tccttgtgct catgtgactt tgtgaaccat taatagtaac    180
cactttgtgc ttgtgtgtgt gtgggcacct gtgtttctgt aatggtctat ctggagtgaa    240
tatatacaag acaggtttgc ctaa                                            264
```

```
<210> SEQ ID NO 14
<211> LENGTH: 332
<212> TYPE: DNA
<213> ORGANISM: Brachypodium distachyon

<400> SEQUENCE: 14
gatgcacgcg acgcgctgct gcttgtggtg tgtgtttgtg tgatctcgac tgaataaaag     60
ggacacggta catccggggt tggttggtgc tcgagtcgag tgtgcaaggt tgtgtggttt    120
gccagctctt ggtgtgtgtc tccttgtgct catgtgactt tgtgaaccat taatagtaac    180
cactttgtgc ttgtgtgtgt gtgggcacct gtgtttctgt aatggtctat ctggagtgaa    240
tatatacaag acaggtttgc ctaaccatgc cttttccttc cttgaggtca tcgcgccaac    300
acgaatgacg agaaccaatg atcttaggac ta                                   332
```

```
<210> SEQ ID NO 15
<211> LENGTH: 630
<212> TYPE: DNA
<213> ORGANISM: Brachypodium distachyon

<400> SEQUENCE: 15
gatgcacgcg acgcgctgct gcttgtggtg tgtgtttgtg tgatctcgac tgaataaaag     60
```

| | |
|---|---|
| ggacacggta catccggggt tggttggtgc tcgagtcgag tgtgcaaggt tgtgtggttt | 120 |
| gccagctctt ggtgtgtgtc tccttgtgct catgtgactt gtgaaaccat taatagtaac | 180 |
| cactttgtgc ttgtgtgtgt gtgggcacct gtgtttctgt aatggtctat ctggagtgaa | 240 |
| tatatacaag acaggtttgc ctaaccatgc cttttccttc cttgaggtca tcgcgccaac | 300 |
| acgaatgacg agaaccaatg atcttaggac tatcaaatag acaatataac tcagcatgga | 360 |
| gcaatgtact gctaatgaac ggtcctaatc aatacagttg ggaagcagta atcgatggaa | 420 |
| aacacttcct cagttcagaa gggaacatgt agatgggaaa gtaaacagga tatatagaca | 480 |
| catgcagtta ggtctaccac aagaagacat gccacaggac taaaaacaga agctgggttt | 540 |
| ggaacaactt atgcagacgc tagctatcca gataaacctt agagaaacag ctatgagaat | 600 |
| aagcgtctga aatttgtagt tgcctgtttg | 630 |

```
<210> SEQ ID NO 16
<211> LENGTH: 727
<212> TYPE: DNA
<213> ORGANISM: Brachypodium distachyon

<400> SEQUENCE: 16
```

| | |
|---|---|
| gatgcacgcg acgcgctgct gcttgtggtg tgtgtttgtg tgatctcgac tgaataaaag | 60 |
| ggacacggta catccggggt tggttggtgc tcgagtcgag tgtgcaaggt tgtgtggttt | 120 |
| gccagctctt ggtgtgtgtc tccttgtgct catgtgactt gtgaaaccat taatagtaac | 180 |
| cactttgtgc ttgtgtgtgt gtgggcacct gtgtttctgt aatggtctat ctggagtgaa | 240 |
| tatatacaag acaggtttgc ctaaccatgc cttttccttc cttgaggtca tcgcgccaac | 300 |
| acgaatgacg agaaccaatg atcttaggac tatcaaatag acaatataac tcagcatgga | 360 |
| gcaatgtact gctaatgaac ggtcctaatc aatacagttg ggaagcagta atcgatggaa | 420 |
| aacacttcct cagttcagaa gggaacatgt agatgggaaa gtaaacagga tatatagaca | 480 |
| catgcagtta ggtctaccac aagaagacat gccacaggac taaaaacaga agctgggttt | 540 |
| ggaacaactt atgcagacgc tagctatcca gataaacctt agagaaacag ctatgagaat | 600 |
| aagcgtctga aatttgtagt tgcctgtttg gaatggctta tggacgacaa gcttattttc | 660 |
| tggagtagcc tacaagtaca agccaaggca catgctgttc caaactggcc catattttgc | 720 |
| acaacca | 727 |

```
<210> SEQ ID NO 17
<211> LENGTH: 1000
<212> TYPE: DNA
<213> ORGANISM: Artificial Sequence
<220> FEATURE:
<223> OTHER INFORMATION: Modified version of the Brachypodium distachyon
      metallothionein-like gene (mtl)  3'-UTR

<400> SEQUENCE: 17
```

| | |
|---|---|
| gatgcacgcg acgcgctgct gcttgtggtg tgtgtttgtg tgatctcgac tgaataaaag | 60 |
| ggacacggta catccggggt tggttggtgc tcgagtcgag tgtgcaaggt tgtgtggttt | 120 |
| gccagctctt ggtgtgtgtc tccttgtgct catgtgactt gtgaaaccat taatagtaac | 180 |
| cactttgtgc ttgtgtgtgt gtgggcacct gtgtttctgt aatggtctat ctggagtgaa | 240 |
| tatatacaag acaggtttgc ctaaccatgc cttttccttc cttgaggtca tcgcgccaac | 300 |
| acgaatgacg agaaccaatg atcttaggac tatcaaatag acaatataac tcagcatgga | 360 |
| gcaatgtact gctaatgaac ggtcctaatc aatacagttg ggaagcagtc agaagggaac | 420 |

```
atgtagatgg gaaagtaaac aggatatata gacacatgca gttaggtcta ccacaagata        480
tatatacaag acaggtttgc ctaatccatg ccacaggact aaaaacagaa gctgggtttg        540
gaacaactta tgcagacgct agctatccag ataaaccttta gagaaacagc tatgagaata       600
agcgtctgaa atttgtagtt gcctgtttgg aatggcttat ggacgacacg taattttctg        660
gagtagccta caagtacaag ccaaggcaca tgctgttcca aactggccca tattttgcac        720
aaccaaagga aaagagacag tgacataaga gcatctccag tgattcagtg agataccca        780 aagtcatcca aatgtccgtt tcggccgaaa tggacatgct ggccagaaaa acatctccca       840
atgggcgatc ccaaatagat attttgtatg ttttgtccgg cccaatcccc aaacatctcc       900
taaatttggg gcaactttgc ggtgtccagt gtccggtgtc cgggcccact tctttttctc       960
ccaagcgagc atcttcctcc cgaagcacga agcccccgtc                             1000

<210> SEQ ID NO 18
<211> LENGTH: 1001
<212> TYPE: DNA
<213> ORGANISM: Artificial Sequence
<220> FEATURE:
<223> OTHER INFORMATION: Modified version of a Brachypodium distachyon
      metallothionein-like gene (mtl)  3'-UTR

<400> SEQUENCE: 18
gatgcacgcg acgcgctgct gcttgtggtg tgtgtttgtg tgatctcgac tgaataaaag        60
ggacacggta catccggggt tggttggtgc tcgaagttgg tgtgcaaggt tgtgtggttt       120
gccagctctt ggtgtgtgtc tccttgtgct catgtgactt gtgaaaccat taatagtaac       180
cactttgtgc ttgtgtgtgt gtgggcacct gtgtttctgt aatggtctat ctggagtgaa       240
tatatacaag acaggtttgc ctaaccatgc cttttccttc cttgaggtca tcgcgccaac       300
acgaatgacg agaaccaatg atcttaggac tatcaaatag acaatataac tcagcatgga       360
gcaatgtact gctaatgaac ggtcctaatc aatacagttg ggaagcagta atgtggaaaa       420
cacttcctca gttcagaagg gaacatgtag atgggaaagt aaacaggata tatagacaca       480
tgcagttagg tctaccacaa gacatgccac aggactaaaa acagaagctg ggtttggaac       540
aacttatgca gactgctatc cagataaacc ttagagaaac agctatgaga ataagcgtct       600
gaaatttgta gttgcctgtt tggaatggct tatggacgac aatgagtgta ttttctggag       660
tagcctacaa gtacaagcca aggcacatgc tgttccaaac tggcccatat tttgcacaac       720
caaaggaaaa gagacagtga cataagagca tctccagtga ttcagtgaga taccccaaag       780
tcatccaaat gtccgtttcg gccgaaatgg acatgctggc cagaaaaaca tctcccaatg       840
ggtctaacac cccaaataga tattttgtat gttttgtccg gcccaatccc caaacatctc       900
ctaaatttgg ggcaactttg cggtgtccag tgtccggtgt ccgggcccac ttctttttct       960
cccaagcgag catcttcctc cgaagcacg aagcccccgt c                           1001
```

What is claimed is:

1. A nucleic acid vector comprising a promoter operably linked to:
   a) a polylinker sequence;
   b) a non metallothionein-like heterologous coding sequence; or
   c) a combination of a) and b);
wherein said promoter comprises a polynucleotide sequence that has at least 97% sequence identity with SEQ ID NO:1, and said promoter has below ground tissue preferred expression.

2. The nucleic acid vector of claim 1, wherein said promoter is 2.0 Kb in length.

3. The nucleic acid vector of claim 1, wherein said promoter consists of a polynucleotide sequence that has at least 97% sequence identity with SEQ ID NO:1.

4. The nucleic acid vector of any one of claims 1-3, further comprising a sequence encoding a selectable maker.

5. The nucleic acid vector of claim 1, wherein said promoter is operably linked to a heterologous coding sequence.

6. The nucleic acid vector of claim 5, wherein the heterologous coding sequence encodes a selectable marker, an insecticidal resistance protein, a small RNA molecule, a site specific nuclease protein, a herbicide tolerance protein, a nitrogen use efficiency protein, a water use efficiency protein, a nutritional quality protein or a DNA binding protein.

7. The nucleic acid vector of any of claims 1-3, or 5, further comprising a 3' untranslated polynucleotide sequence comprising SEQ ID NO:3, wherein the 3' untranslated sequence is operably linked to said polylinker or said heterologous coding sequence.

8. The nucleic acid vector of any of claims 1-3 or 5, further comprising a 5' untranslated sequence.

9. The nucleic acid vector of any of claims 1-3 or 5, further comprising an intron sequence.

10. A non-*Brachypodium* plant comprising a polynucleotide sequence that has at least 97% sequence identity with SEQ ID NO:1 operably linked to a heterologous coding sequence, wherein said heterologous coding sequence has below ground tissue preferred expression.

11. The plant of claim 10, wherein said plant is selected from the group consisting of maize, wheat, rice, *sorghum*, oats, rye, bananas, sugar cane, soybean, cotton, *Arabidopsis*, tobacco, sunflower, and canola.

12. The plant of claim 10, wherein said plant is maize.

13. The plant of any one of claims 10-12, wherein the heterologous coding sequence is inserted into the genome of said plant.

14. The plant of claim 10, further comprising a 3' untranslated sequence comprising SEQ ID NO:3, wherein the 3' untranslated sequence is operably linked to said heterologous coding sequence.

15. The plant of claim 10, wherein said promoter is 2.0 Kb in length.

* * * * *